United States Patent
Neta

(10) Patent No.: US 11,957,521 B2
(45) Date of Patent: Apr. 16, 2024

(54) DEVICES AND/OR METHODS FOR INSPECTING AND/OR ILLUMINATING A HUMAN EYE

(71) Applicant: Uri Neta, Koranit (IL)

(72) Inventor: Uri Neta, Koranit (IL)

( * ) Notice: Subject to any disclaimer, the term of this patent is extended or adjusted under 35 U.S.C. 154(b) by 0 days.

(21) Appl. No.: 17/800,082

(22) PCT Filed: Feb. 16, 2021

(86) PCT No.: PCT/IB2021/051302
§ 371 (c)(1),
(2) Date: Aug. 16, 2022

(87) PCT Pub. No.: WO2021/165831
PCT Pub. Date: Aug. 26, 2021

(65) Prior Publication Data
US 2023/0090020 A1 Mar. 23, 2023

Related U.S. Application Data

(60) Provisional application No. 62/977,859, filed on Feb. 18, 2020.

(51) Int. Cl.
*G02B 21/00* (2006.01)
*A61B 90/35* (2016.01)
*A61F 9/007* (2006.01)
*G02B 21/06* (2006.01)
*A61B 90/30* (2016.01)

(52) U.S. Cl.
CPC .............. *A61B 90/35* (2016.02); *A61F 9/007* (2013.01); *G02B 21/0012* (2013.01); *G02B 21/06* (2013.01); *A61B 2090/306* (2016.02)

(58) Field of Classification Search
CPC . A61B 90/35; A61B 2090/306; A61B 3/0091; A61B 3/13; A61B 3/102; A61B 3/1225; A61F 9/007; G02B 21/0012; G02B 21/082; G02B 21/025; G02B 21/06; G02B 21/095; G02B 21/10; G02B 21/18; G02B 21/20
See application file for complete search history.

(56) References Cited

U.S. PATENT DOCUMENTS

| 7,058,255 B1 | 6/2006 | Fang | |
|---|---|---|---|
| 2004/0227989 A1* | 11/2004 | Obrebski | A61B 3/13 359/388 |
| 2009/0323023 A1 | 12/2009 | Kogawa et al. | |
| 2014/0092362 A1* | 4/2014 | Narayanaswamy | G02B 21/06 351/221 |
| 2014/0152959 A1* | 6/2014 | Kuster | G02B 21/10 351/221 |
| 2016/0081545 A1 | 3/2016 | Hauger et al. | |
| 2016/0150953 A1 | 6/2016 | Sasaki et al. | |
| 2017/0340483 A1 | 11/2017 | Rill et al. | |

\* cited by examiner

*Primary Examiner* — Mustak Choudhury
(74) *Attorney, Agent, or Firm* — The Law Office of Joseph L. Felber

(57) ABSTRACT

An optic system assists visualization of eye elements during ophthalmic surgery. The system has optic devices aimed at affecting light emitted by an ophthalmic microscope for observing an eye during surgery. This affecting can be by selecting the wavelength spectrum of the emitted light, tilting a light path of the emitted light and/or by changing the light path of the emitted light from the source to the eye under surgery.

13 Claims, 22 Drawing Sheets

DEVICES AND/OR METHODS FOR INSPECTING AND/OR ILLUMINATING A HUMAN EYE

TECHNICAL FIELD

Embodiments of the invention relate to devices and/or methods for inspecting and/or illuminating a human eye, in particular during eye surgery.

BACKGROUND

Eye or ocular surgery is performed on the eye or its adnexa normally by an ophthalmologist. One example of eye surgery may be aimed at treating a cataract, which is a clouding of the eye's natural lens. A cataract may prevent light from forming a clear image on the retina and may be due to various reasons such aging, disease, or trauma. In cases where harm to the vision of a patient may be severe, removal of the lens may be required in order to implant a plastic intraocular lens instead of the damaged natural lens.

During eye surgery high intensity white light is typically incident into the patient's eye in order to provide to the surgeon a view of the eye being treated. This may raise problems, such as the following.

A first problem may relate to the fact that in some ophthalmic surgeries permanent damage to a patient's retina may be inflicted due to excess light intensity typically emitted by an ophthalmic microscope used by the ophthalmologist onto the patient's retina. This sometimes may be called light toxicity.

In many cases, a surgeon performing the operation doesn't know which patient may be susceptible to permanent damage and what may be the limit of intensity that may inflict such damage. In many cases, a surgeon may have his/her own preset light parameters for suitable illumination for surgery. The light power incidence on the pupil may be about 100 [$\mu W/mm^2$] at visible wavelengths from about 400 to about 700 [nm].

Another problem that may arise relates to insufficient background illumination in red resulting in poor imaging quality during parts of the surgery. This may be in the form of relative low intensity, resolution and contrast—which might lead to complications during surgery, e.g. during cataract surgery fragments of the original lens might be less visible and thus remain within the eye prior to implanting of the plastic lens. This may result in the patient viewing such left-over fragments of the original lens as a dark object within his/her view after surgery for few weeks or months.

In various ocular surgery procedures, enhanced visualization of eye elements being treated, such as the lens region of an eye, may obtained by utilizing light being scattered by such elements.

Various theories propose descriptions of scattering of an electromagnetic plane wave when passing though small particles. The Rayleigh scattering model describes a phenomenon of light scattering from small particles that are smaller in dimension than the light wavelength. The Mie scattering model describes light scattering from small particles that are larger than the light wavelength.

The Mie model describes scattering intensity versus angle and should converge to the Rayleigh scattering model when particles decrease in dimensions. Descriptions of these theories can be found for example in: "Light Scattering Theory" David W. Hahn, Department of Mechanical and Aerospace Engineering, University of Florida.

SUMMARY

The following embodiments and aspects thereof are described and illustrated in conjunction with systems, tools and methods which are meant to be exemplary and illustrative, not limiting in scope.

In a broad aspect, embodiments of the present invention may be defined as aimed at providing a surgeon with a better view of an eye being treated/operated so that he/she can do better and safer in an interventional procedure being conducted to the eye.

In one example, this may be accomplished by providing an ophthalmic surgeon with an optic system (e.g. for cataract surgery) that assists in providing a surgeon with views of a patient's eye that have increased resolution, brightness and contrast—while using lower light intensities to illuminate the eye relative to light intensities typically used in such procedures.

At least certain embodiments may be defined as providing an illumination system that alters the spectrum of light entering an eye e.g. during surgery. In some embodiments, such illumination system may include a spectral light source that is arranged to generate illumination that can be directed along a path that is generally coaxial to an optic axis of a 'visualization device', such as an ophthalmic microscope, a 3D surgical digital and/or video microscope (or the like); to which it can be externally or internally attachable. From hereon, use of the term ophthalmic microscope should be understood in its broadest sense to refer to one or more of the above 'visualization device' types. An example of a 3D video digital microscope may be e.g. the TrueVision 3D Visualization system, the ORBEYE 3D Visualization System of Olympus, the Zeiss-Artevo 800.

The illumination generated by such optic system embodiments may be arranged to provide background illuminating of an eye with increased brightness while utilizing an illumination intensity that may be less than current intensities used by ophthalmic microscopes, e.g. at least 10-fold less (e.g. 50 fold less, 80 fold less) (or the like).

In certain aspects, the present invention may be aimed at providing illumination module embodiments utilizing a blue light source for illuminating an eye. Such illumination modules may be attached/located to a patient near the eye periphery during surgery in order to enhance image details and increase e.g. by about 50% the resolution apparent to the surgeon (e.g. increase the ability to detect details inside the eye of about 15 micron in size from about 30 micron in size under white light). Such increase in imaging quality has been observed in experiments conducted during actual eye surgeries and on an eye optical model with resolution target inside the capsule.

In certain embodiments, this may be accomplished by way of providing an ophthalmic surgeon with a better and sharper view of eye elements on the one hand, while eliminating or at least substantially reducing danger of inflicting light toxicity (permanent damage to retina due to high light intensity incidence on the retina) to the retina of a patient being treated on the other hand.

In at least certain cases, optic system embodiments of the present invention may reduce/limit risk of inflicting light toxicity to an eye, by utilizing a light source emitting wave lengths in a spectrum generally similar to that scattered back from the retina (in particular macula).

Optic systems of the present invention, may be adapted for use with an ophthalmic visualization device such as a microscope (or the like) and may be embodied as 'auxiliary' or 'integrated' to such microscope. An 'auxiliary' optic system may take form of a standalone arrangement not necessarily forming part of an existing ophthalmic microscope structure. An 'integrated' optic system may in other words be seen being part of an ophthalmic visualization device and by that imparting to such visualization device enhanced visualization.

An 'auxiliary' optic system may be arranged to be maneuvered between an aligned state with an optical axis of a microscope or an un-aligned state with an optical axis of a microscope setting it aside from intervening with the optical axis of the microscope.

In an aligned state, light emitted by an internal light source of the microscope may be able to pass through the 'auxiliary' optical system in order to provide background illumination to the eye, or an internal light source of the 'auxiliary' optical system may provide such illumination together or instead. In an un-aligned state, the 'auxiliary' optical system may be set aside not contributing to a procedure underway.

An 'auxiliary' optic system may be attached to an existing ophthalmic visualization device e.g. via an adaptor. An 'integrated' optic system may accordingly be integrated into an ophthalmic visualization device's structure thus forming an 'enhanced' visualization device (e.g. microscope).

Scattered wave length spectrum directed back out of the eye, forms the so-called 'red reflex' wavelength spectrum that provides a surgeon with background and contrast necessary for visualization of eye elements being treated such as the capsule, lens and anterior chamber structure, during ophthalmic surgery. However, at least in certain cases under white light illumination the visualization may not be sufficient.

In certain cases, a light source being used in certain optic system embodiments may emit light including a wavelength spectrum defining red and green light, or in some cases generally limited to a vicinity of a wave length spectrum defining red light.

In at least certain embodiments, an illumination module may be provided for emitting light from adjacently near to the eye being operated in order to enhance resolution and details of eye elements being treated by the surgeon.

In certain cases, such illumination module embodiments may preferably aim incidence light towards the eye at an angle relative to the eye's optical axis.

In certain cases, such illumination modules may form part and/or work in conjunction with at least certain optic system embodiments of the present invention. Such illumination modules may be structured as distinct devices possibly controlled together with an optic system for assisting a surgeon during eye surgery.

In some cases, certain illumination module embodiments may also be utilized in other procedures not necessarily involving an embodiment of an optic system and/or an ophthalmic microscope—such as in Retina surgery.

Certain illumination module embodiments may be arranged to emit light including a wave length spectrum defining blue light, or in some cases generally limited to a vicinity of a wave length spectrum defining blue light.

Certain system or module embodiments may include a control system for controlling each device independently or in conjunction with each other.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which.

Figure 1:
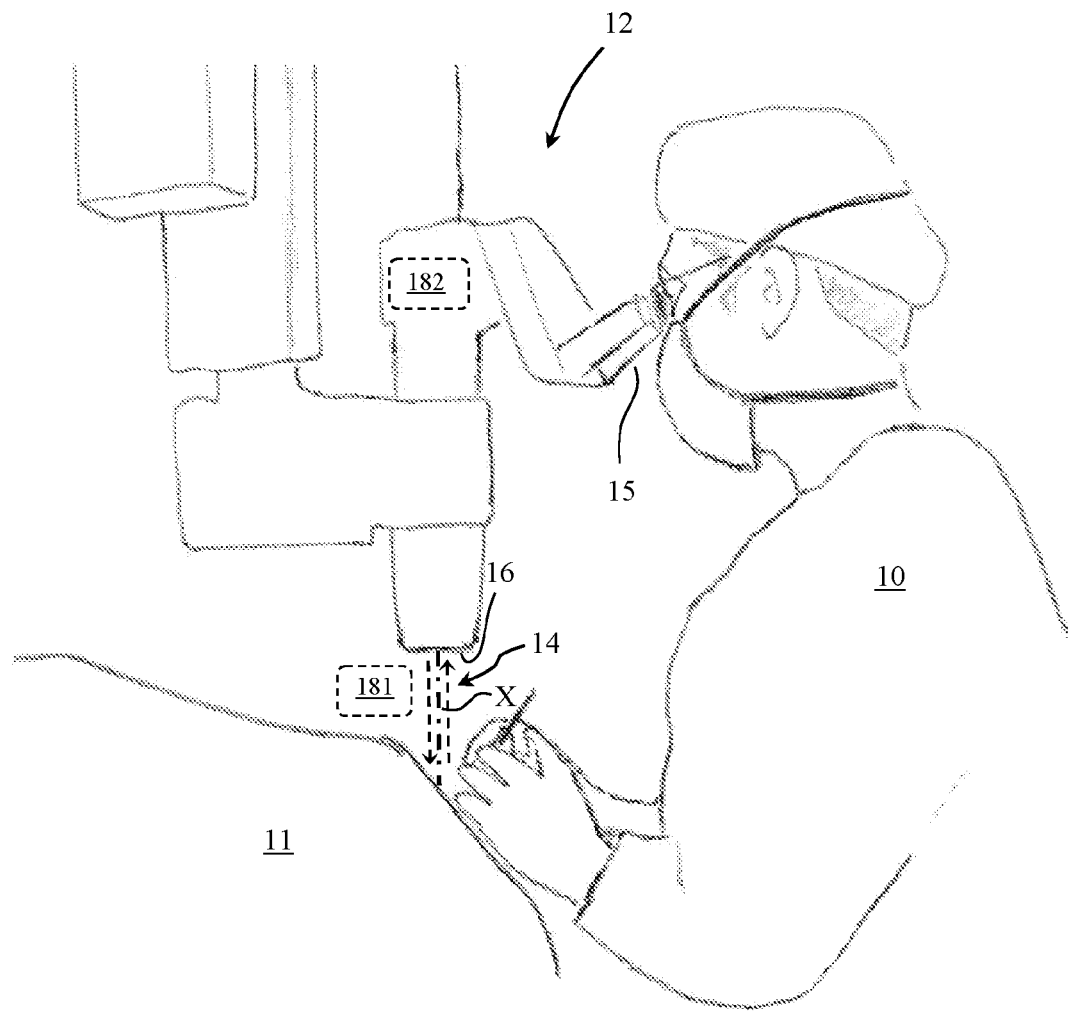
FIG. 1 schematically shows a surgeon conducting an eye surgery using an ophthalmic microscope.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Attention is first drawn to FIG. 1 showing a surgeon 10 conducting an eye surgery to a patient 11 (here concealed by a covering) using an ophthalmic microscope 12. It is noted that an ophthalmic microscope as used herein may refer to any visualization device type typically used during ophthalmic surgery, such as the ARTEVO 800 Digital Microscope of Carl ZEISS Meditec AG, the 3D Surgical Microscope of SOMETECH Co., Ltd, Zeiss-Lumera-700, Leica-F-40 (or the like). Microscope 12 has an optical axis X along which at least part of a light path 14 outside of the microscope (see marked by dashed arrows) can be seen formed along the axis X.

Light within light path 14 is emitted away and back towards the microscope passing, inter alia, through an objective lens 16 of the microscope, which is the closest optical element of the microscope to the patient being treated. The surgeon may view scenes located along optical axis X and light path 14 via an eyepiece 15 of the microscope.

The surgery procedure here illustrated and discussed herein below will be a cataract surgery, however embodiments disclosed herein may be equally applicable to other procedures that utilize reflex background illumination—such as retina surgery.

Figure 2A:
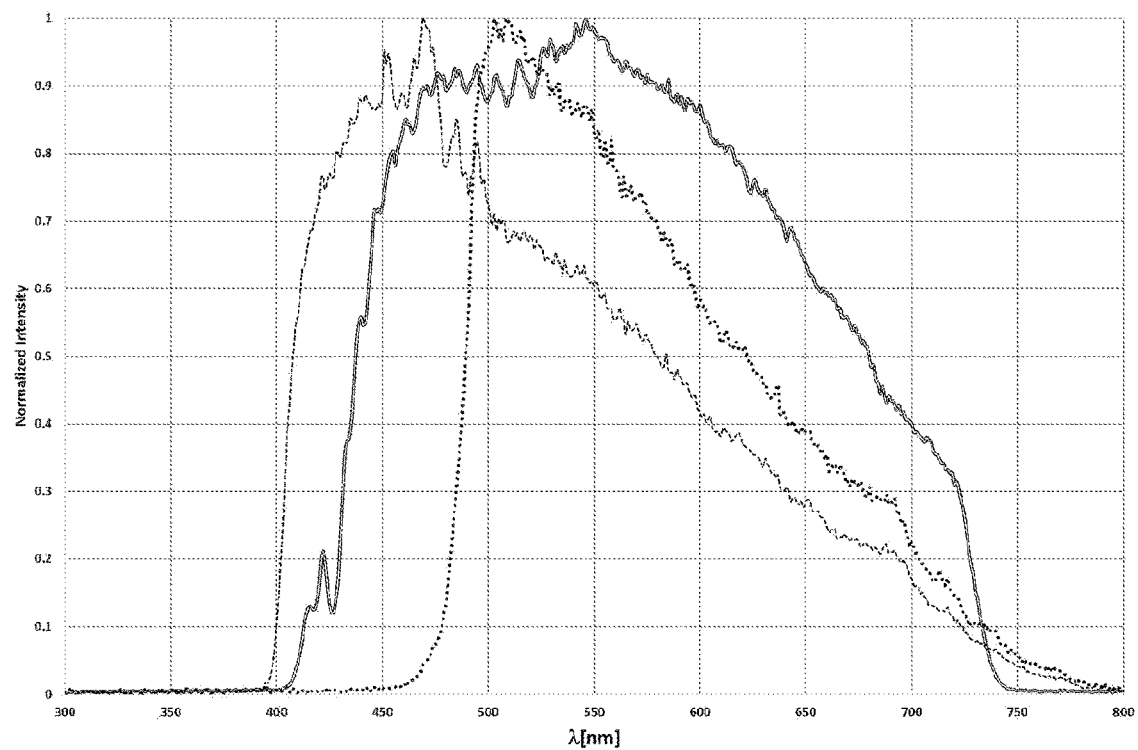
FIGS. 2A and 2B respectively show emitted wavelength spectrums of typical ophthalmic microscopes that are directed into a patient's eye; and a typical red reflex wavelength spectrum of light scattered back from the retina to the surgeon for providing background illumination necessary for visualization of e.g. the capsule, lens and anterior chamber structure, during ophthalmic surgery.

Attention is drawn to FIG. 2A illustrating emitted wavelength spectrums of typical ophthalmic microscopes and modes of illumination that are directed into a patience eye (such as Zeiss-Lumera-700-Retina, Zeiss-Lumera-700-LED, Leica-F-40-Main).

Figure 2B:
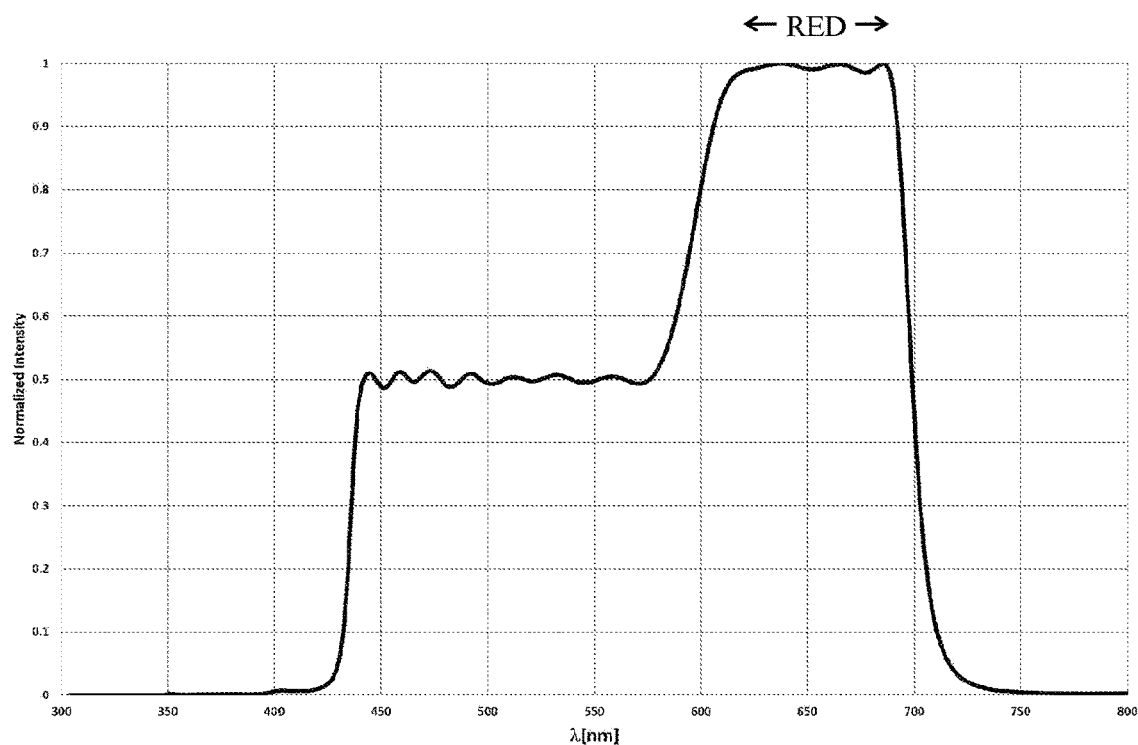

FIG. 2B shows an example of red reflex wavelength spectrum of light reflected back from the retina (in particular macula) to the surgeon for providing background illumination necessary for visualization during ophthalmic surgery of eye elements such as the capsule, lens, anterior chamber structure (and the like). The graph as shown in FIG. 2B is merely an example, and such scattered red-flex wave spectrum may vary slightly from patient to patient.

As apparent, these exemplary figures show that while typically emitted wave length spectrums may cover a large spectrum of waves lengths, such as substantially the entire visible spectrum of waves lengths from about 380 to about 740 nanometers (FIG. 2A)—the red reflex wave length spectrum providing the surgeon with the background and contrast of the eye is in a smaller range as seen in this illustration from about 440 to about 750 nanometers (FIG. 2B).

The red reflex wave length spectrum can be seen substantially peaking in the red spectrum from about 600 to about 750 nanometers, and in this example the intensity of the peaking back scattered red reflex is about twice that of the remaining other back scattered wavelengths from about 440 to about 570 nanometers.

Figure 3A:
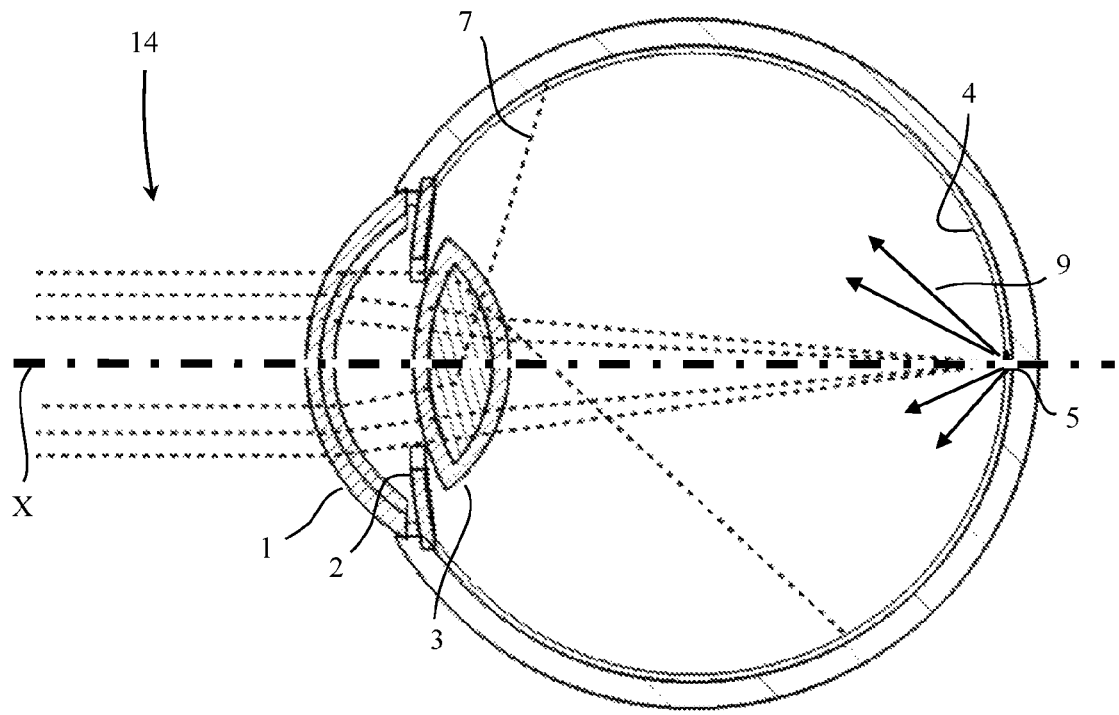
FIGS. 3A to 3D schematically show light rays emitted into an eye and scattered back from parts of the eye during various stages of a cataract surgery.
Figure 3B:
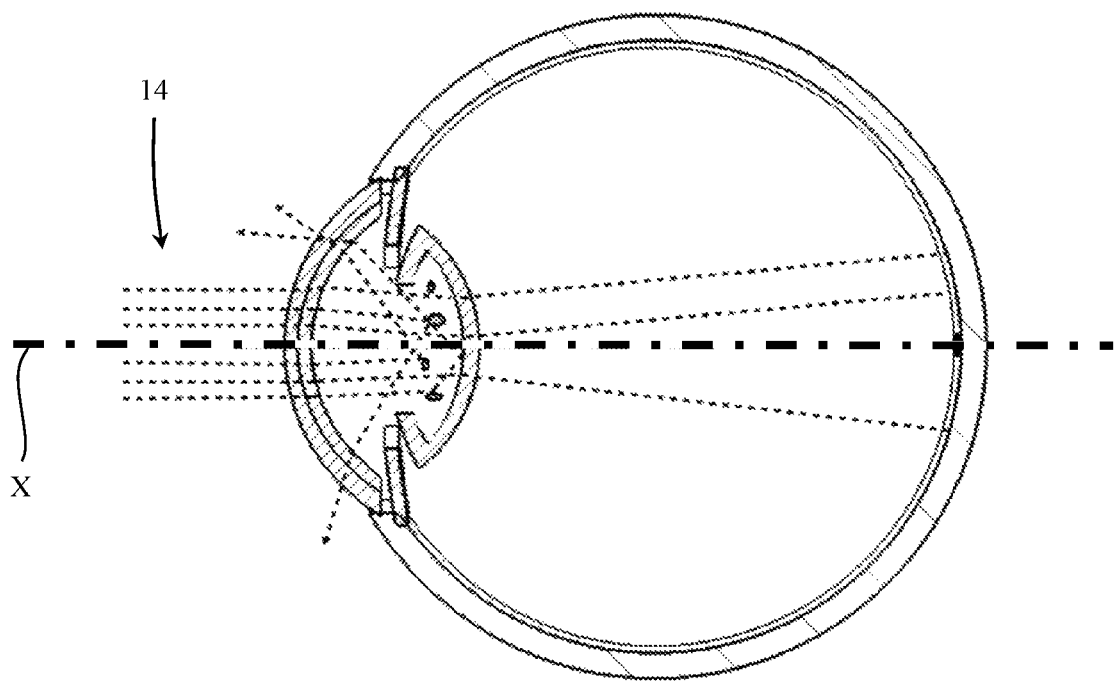

Attention is drawn to FIGS. 3A and 3B illustrating optic paths that incoming and outgoing light rays passing along the microscope's optic axis X may traverse during surgery, in this example cataract surgery aimed at replacing a damaged natural lens in an eye with an implanted plastic intraocular lens.

FIG. 3A illustrates light ray paths before e.g. start of cataract surgery. Incoming light can be seen arriving along light path 14, e.g. from a light source of an ophthalmic microscope (such as 12 seen in FIG. 1) and along an optical axis of said microscope (such as X indicated in FIG. 1). The incoming light passes through the cornea 1, open iris 2 and lens 3 which, inter alia, assists in focusing the incoming light towards the retina 4 and specifically the macula 5 which is a small area of about 20 square millimeters of high-density vision cells (like cone and rode).

The light rays arriving at the retina (in particular macula) are then scattered in various directions 9 with a substantial amount of light being directed by assistance of the eye's lens back out of the eye through the open iris. This outgoing light, which illuminates mainly in red eye elements such as the lens, lens capsule (etc.), travels along optical axis X and light path 14 back towards the microscope to eventually arrive at the surgeon's eyes observing the surgical procedure via eyepiece 15 (see FIG. 1). Some rays 7 can be seen in this example being scattered due to cataract (scattering centers in the original lens).

In some cases, excess light intensity used by a surgeon for illuminating the eye may result in damage to the retina known as 'light toxicity'. Thus, an independent aspect of at least certain embodiments of the present invention may be defined as reducing exposure of the eye to relative high light intensities while substantially not compromising and possibly also enhancing the quality of visualization of the eye to a surgeon conducting a surgical procedure to the eye.

The above may be accomplished by eliminating at least some of the wavelengths found as ineffective in providing the 'red reflex' wave length spectrum (while possibly changing the ratio of intensity of the relevant wavelength) from light spectrum being projected into the eye during surgery to thereby form a lower intensity 'operative-spectrum' used for illuminating the eye.

In one example, such 'operative-spectrum' being projected into the eye may be substantially in wavelength values identified as those scattered by the retina (in particular macula) as depicted in FIG. 2B. In one example, such 'operative-spectrum' may be defined as being between about 430 to about 700 nanometers, with a first sub-range from about 600 to about 700 nanometers and possibly also in a second sub-range from about 430 to about 600 nanometers, while the intensity in the first sub-range may be chosen to be substantially larger (e.g. about twice) that in the second sub-range.

Attention is drawn to FIG. 3B. Once commencing removal of the natural eye lens at least partially, the focal power of the natural lens formerly assisting in directing light rays towards the retina and in particular the macula—is reduced dramatically (e.g. by at least a factor of two in intensity). This as seen may result in substantially less light rays hitting the macula to be scattered back towards the area of the lens being treated in order to illuminate it. Thus, the image the surgeon may be provided with during this critical step, may be substantially dim and in relative low contrast and resolution (which may result e.g. in fragments of the original lens being left within the eye after surgery is completed and other complications related to resolution and contrast of the surgeon's eye).

Consequently, the surgeon operating the eye may be provided with lower background illumination that may affect his/her ability to successfully conduct the surgical procedure taking place. Further shown in this figure is that at least some of the incoming light may be scattered or absorbed by fragments left within the treated eye and by that diverge away light from a direct path towards the macula further reducing visualization for the surgeon.

Figure 3C:
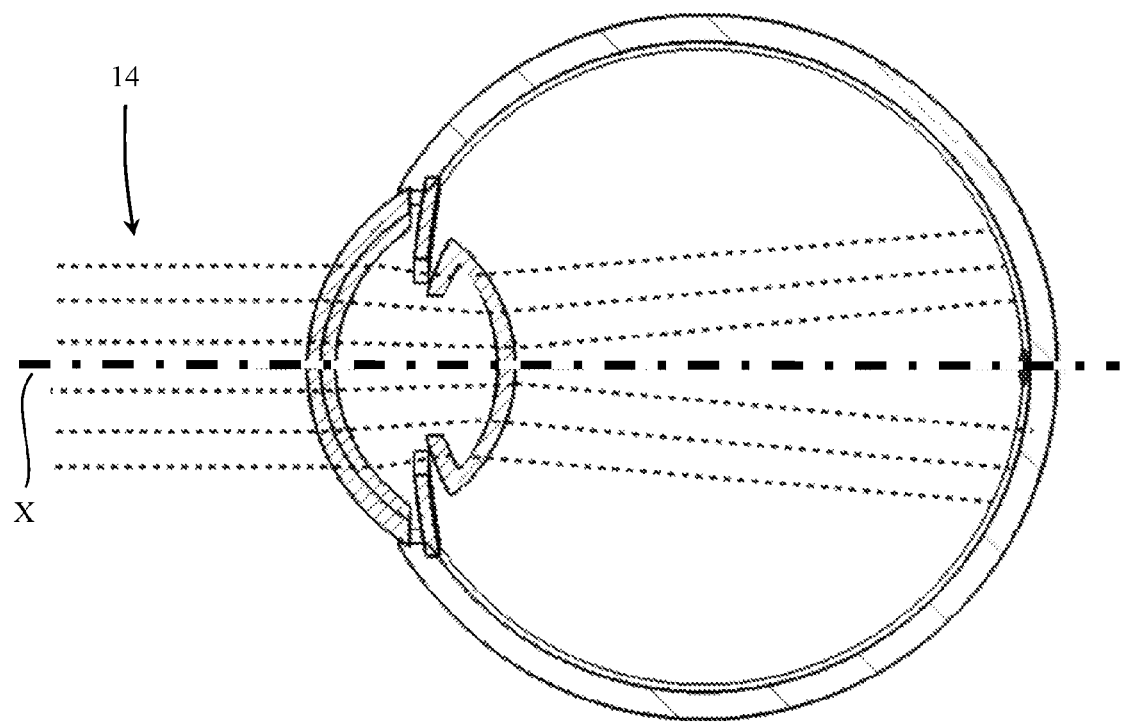
Figure 3D:
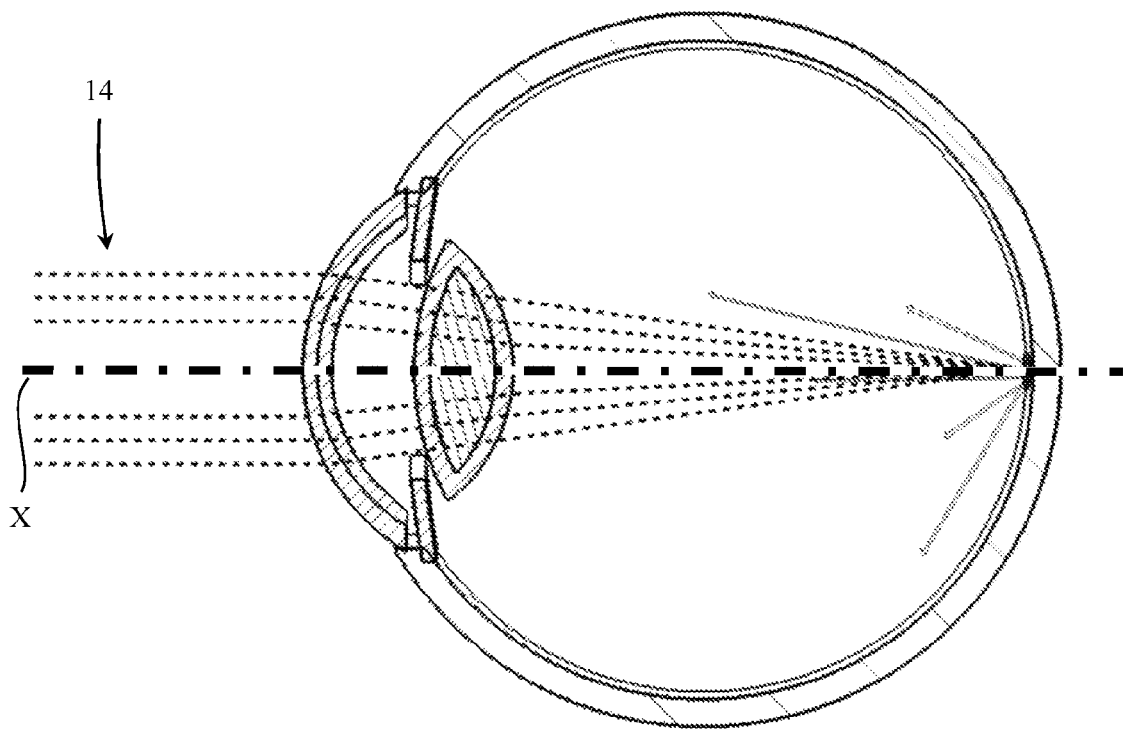

FIG. 3C depicts the eye after removal of substantially all of the natural lens—and as seen the light in this state of the eye is not focused towards the macula. This is typically a critical step during surgery were the surgeon preferably seeks for leftover fragments of e.g. the original eye lens, however due to dim background illumination (Reflex) intensity and bad resolution and contrast—this activity may be compromised. FIG. 3D illustrates the eye after a plastic intraocular lens has been successfully implanted into the lens capsule, which resumes a repaired eyesight for the patient whereby incoming light is focused at the retina and in particular macula.

An additional situation that may occur during surgery, in which incoming light may be shifted away from being focused towards a vicinity the macula, may be due to movement of the eye caused e.g. as the surgeon presses surgical tools against the eye. The eye in such situation may e.g. rotate slightly and by that rotate the macula from being aligned with the microscope's optical axis X along which the incoming light travels. Such a situation can be seen in FIG. 5D that will be discussed herein below in the context of FIG. 5.

An independent aspect of at least certain embodiments of the present invention may thus be related to 'focal-corrections' aimed at maintaining e.g. incoming light focused at the eye's retina and in particular a vicinity of the macula. It is noted that this independent aspect may be combinable if desired with the former independent aspect of reducing likelihood to light toxicity by projecting into the eye an 'operative-spectrum' of light.

In an embodiment, such 'focal-correction' may be accomplished by an 'intervening lens' that may be arranged to intervene with incident light emitted towards the eye in order to restore during surgery at least part or substantially most of the focal power lost due to removal of the eye's natural lens—so that light entering the eye may substantially maintain a focused route targeting a vicinity of the macula during the surgical procedure.

In another embodiment, such 'focal-correction' may be accomplished in addition and/or alternatively to use of an 'intervening lens'—by tilting a light beam used for illuminating the eye, so that incident light of such tilted light beam assumes a modified route that resumes focus towards a vicinity of the macula during movements of the eye. Possible, such "tilting" may be accomplished by introducing an optical wedge into the beam.

The above mentioned independent aspects (i.e. 'operative spectrum', 'intervening lens', 'tilted light beam')—possibly combinable one with the other but not necessarily—may be implemented by utilizing optic systems according to various embodiments of the present invention. Such optic systems may be embodied as so-called 'auxiliary' and/or 'integrated' with an ophthalmic visualization device such as an ophthalmic microscope used for eye surgery.

With attention drawn back to FIG. 1, where an 'auxiliary' type optic system according to various embodiments of the present invention can be seen marked by numeral 181; and an 'integrated' type optic system according to various embodiments of the present invention can be seen marked by numeral 182.

Figure 4A:
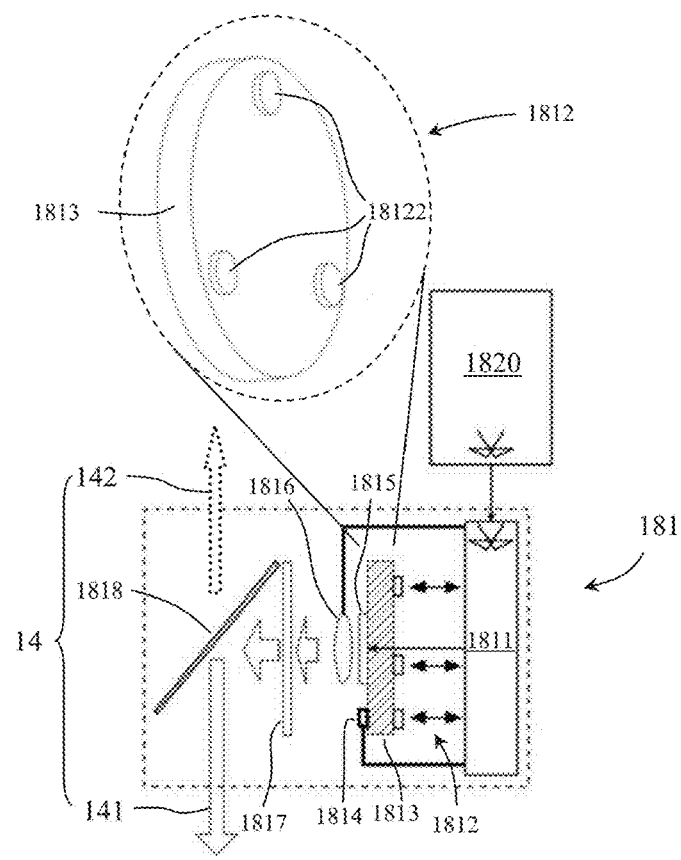
FIGS. 4A to 4C schematically show an auxiliary optic system in accordance with various embodiments of the present invention for assisting in inspection of a patient's eye during an eye surgery.
Figure 4A:
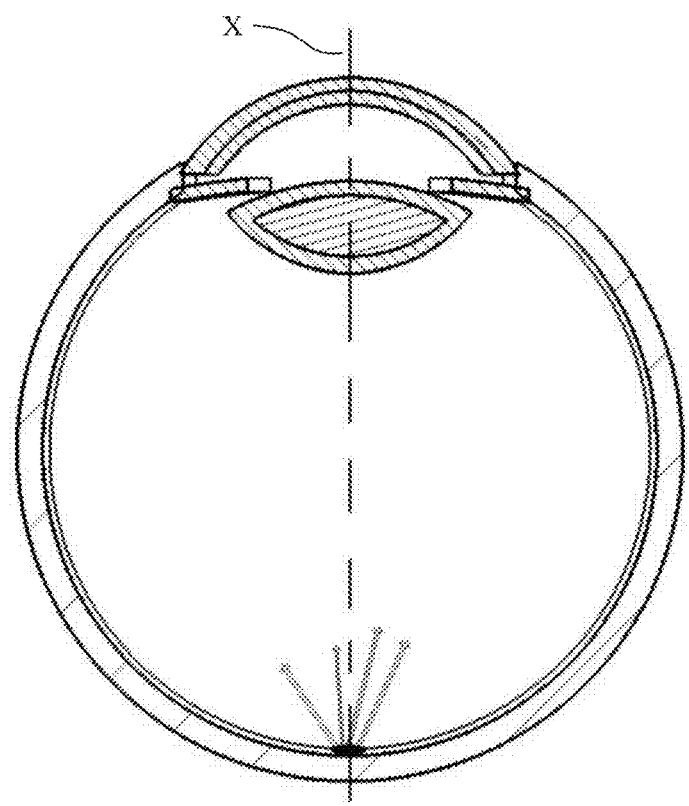

Attention is drawn to FIG. 4A illustrating an embodiment of an 'auxiliary' optic system 181. Auxiliary optic system 181 in this example can be seen including a light controller 1811, an actuator 1812, a heat sink 1813, a feedback sensor 1814, a light source 1815, a tunable intervening lens 1816, an optional filter 1817 and a beam splitter 1818. In the enlargement shown at the upper side of this figure, actuator 1812 can be seen including several (here optionally three) actuating members 18122 in this example coupled upon heat sink 1813.

Auxiliary optic system 181 may be attachable to the microscope possibly by a rotating hinge or the like (not shown) so that it can be urged (e.g. rotated) into and/or out of intervention with light path 14.

Light controller 1811 may be arranged to control operation of light source 1815, which may in turn be in the form of a COB LED (or the like). Light source 1815 may be mounted in thermal contact with heat sink 1813.

Light emitted by light source 1815 may be arranged to initially follow a route that may be transverse (e.g. generally orthogonal but not necessarily) to an optical axis X of a microscope with which it cooperates (the microscope not being shown in FIG. 4). Beam splitter 1818 may be positioned to intercept optical axis X and may be placed at an angle that is suitable to reflect light emitted by light source 1815 in this view downwards along optical axis X towards the eye being treated. This portion of the light being reflected along light path 14 towards the eye is indicted in FIG. 4 by numeral 141.

Light emitted by auxiliary optic system 181 may be in various spectrums such as those illustrated in FIG. 2A. In certain cases, light emitted by auxiliary optic system 181 may in an 'operative-spectrum' (such as that shown in FIG. 2B) that is less likely to inflict light toxicity to an eye being treated.

In certain embodiments, this may be accomplished by using a light source 1815 that is designed to emit an 'operative-spectrum'. In other embodiments, various type light sources 1815 may be used (such as that emitting one of the spectrums seen in FIG. 2A), and such light may be directed to pass through a filter 1817 that may be designed to allow light according to a desired 'operative-spectrum' (such as that shown in FIG. 2B) to pass onwards towards the eye.

Light 141 emitted by auxiliary optic system 181 and entering the eye may be scattered from the retina (in particular macula) with some of this light exiting back out of the eye along axis X. This light exiting back out of the eye forms part of light path 14 and a portion of this light that passes through beam splitter 1818 is indicated in FIG. 4 by numeral 142.

A portion of this light may be directed by beam splitter 1818 into optic system 181 while another portion 142 continues along optical axis X towards the microscope to provide the surgeon with a view of the eye being treated.

In certain embodiments, beam splitter 1818 may be configured to allow a larger percentage of incoming incident light to transmit through it while reflecting a smaller percentage of light. Such configuration of beam splitter 1818 may be useful in allowing a larger percentage of light scattered and reflected back from the eye to arrive into the microscope in order to provide the surgeon with a detailed as possible view of the eye being treated.

In a non-binding example, beam splitter 1818 may be designed to be of a 90/10 type, permitting about 90% of incoming incident light to transmit and pass through it while reflecting about 10% of the light.

In the case where incoming incident light is from light source 1815, about 90% of this light transmits onwards through beam splitter 1818 (and thus does not illuminate the eye) while only about 10% is reflected along axis X into the eye. In the case where the incoming incident light is scattered light reflected back from the eye, about 90% of this light transmits onwards along axis X through beam splitter 1818 towards the microspore while only about 10% is reflected into the auxiliary optic system 181.

Intensity of light arriving back from the eye and reflected into auxiliary optic system 181 by beam splitter 1818 may be sensed by feedback sensor 1814.

Figure 5A:
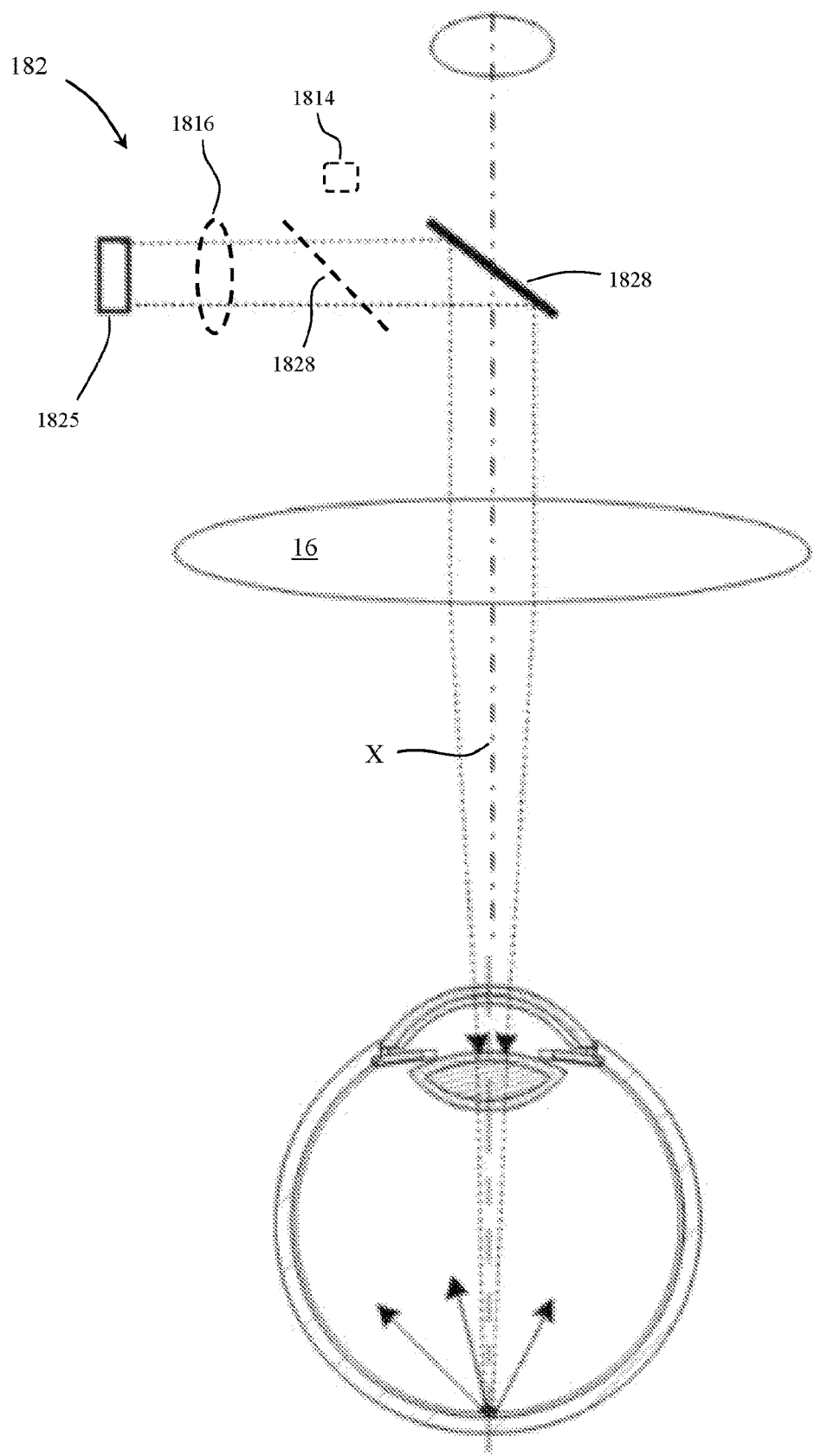
FIGS. 5A to 5G schematically show an integrated optic system in accordance with some embodiments of the present invention, possibly combined into an ophthalmic microscope, where the various figures demonstrate various possible modes of operation of either the integrated or auxiliary system embodiments during eye surgery.
Figure 5B:
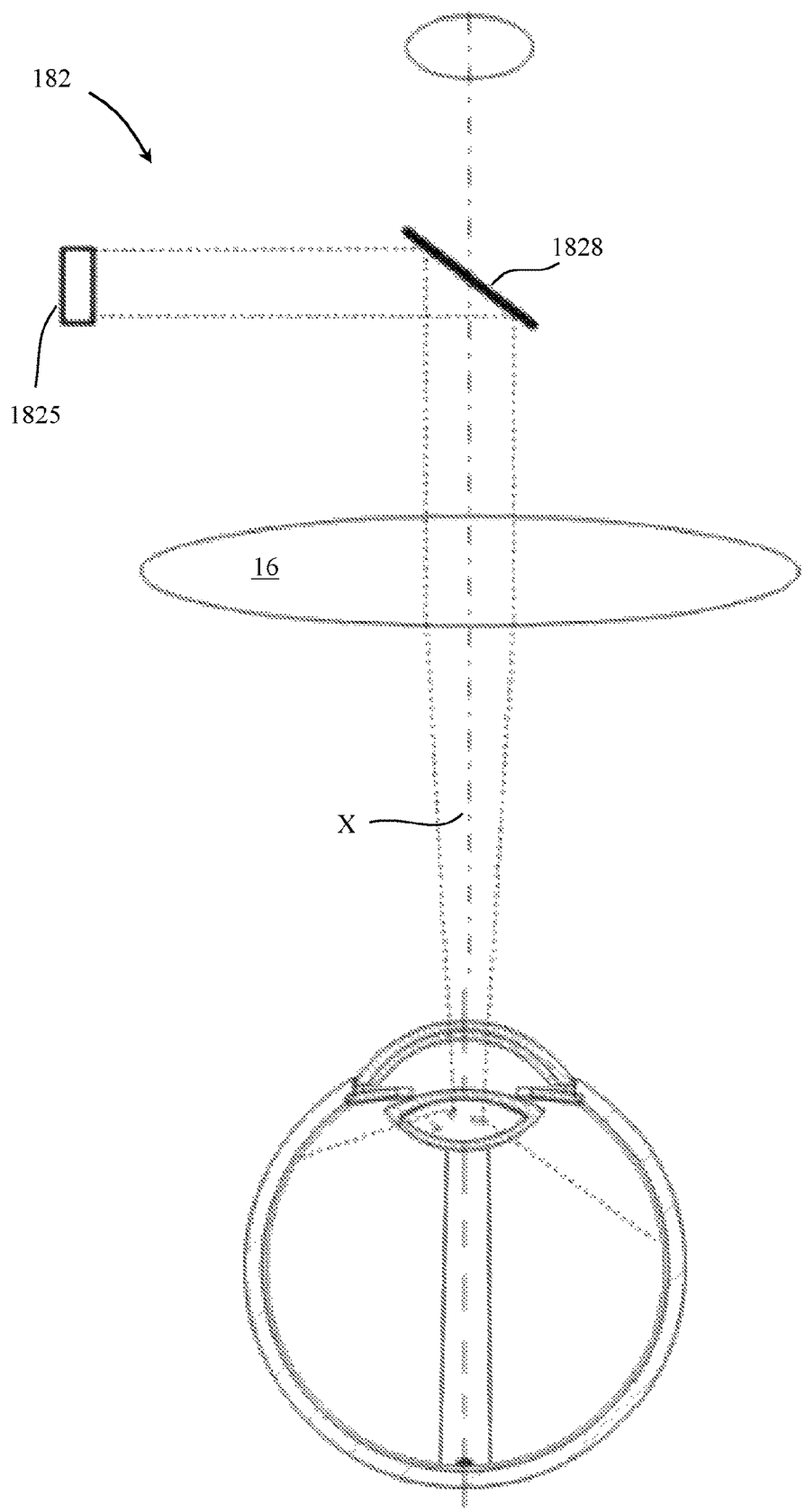
Figure 5C:
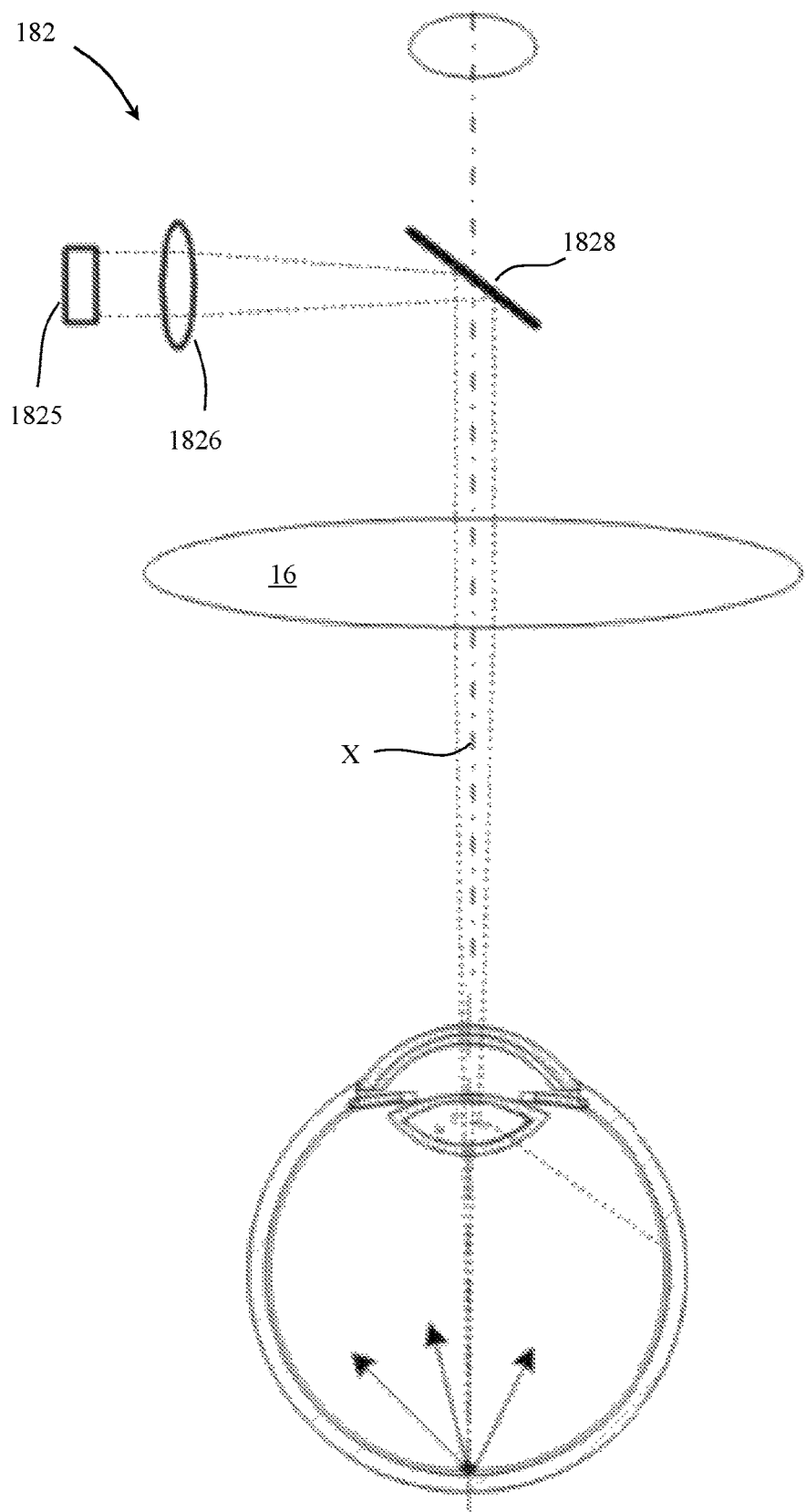
Figure 5D:
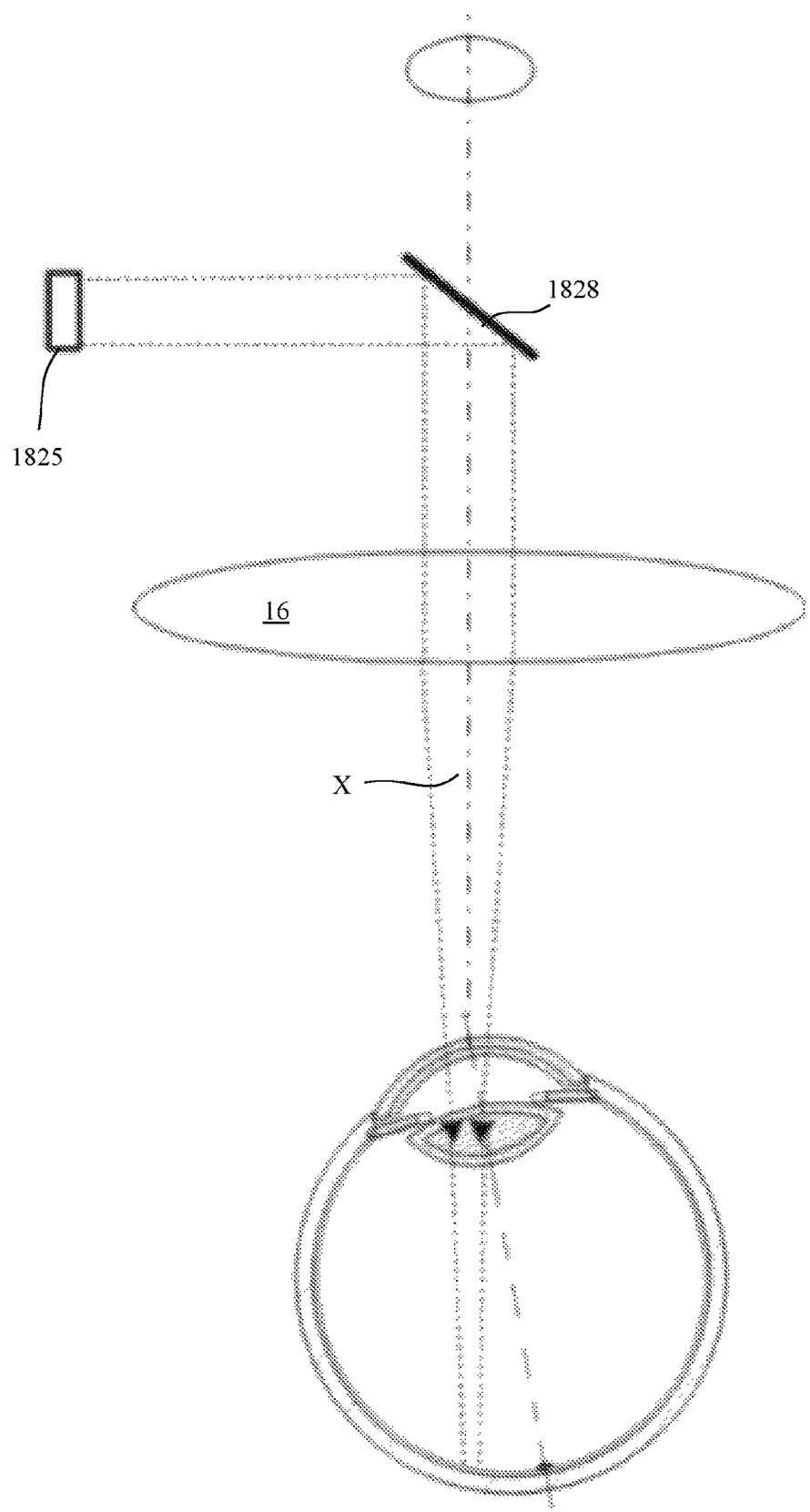

As already discussed, during surgery the eye may move (e.g. rotate as seen in FIG. 5D) and this may in turn result in a drastic decrease in the intensity of the light that is scattered back from the retina to exit the eye. This may accordingly occur since light entering the eye may be diverted by movement of the eye from impacting the retina at a vicinity of the macule (where most back scattering occurs).

Intensity of light detected by feedback sensor 1814 and communicated to controller 1811 may assist in detecting such movement of the eye, by e.g. detecting a drop in the intensity of the light relative to former measurements.

In certain embodiments, auxiliary optic system 181 via controller 1811 that receive such incoming data from sensor

Figure 4B:
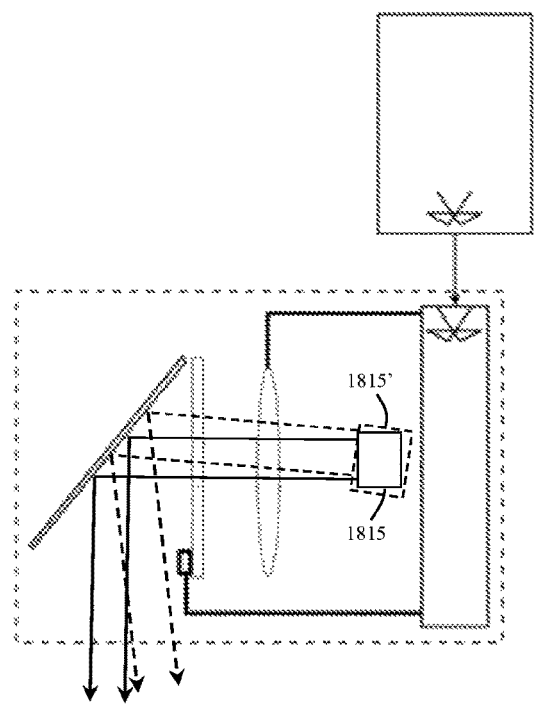

1814—may be arranged tilt light source 1815 be means of an actuator, such as the optional actuator 1812 shown herein. Controller 1811 may trigger one or more of the actuating members 18122 of actuator 1812 to distort and by that urge light source 1815 to tilt. FIG. 4B illustrates such an example of a tilted light beam from a first position (marked as 1815) to a second tilted position (marked as 1815').

The tilting of the light beam causes incident light emitted by the light beam to travel along altering optical paths towards the retina (see optical paths of the dashed lines of tilted position 1815' relative to the solid lines prior to tilting). As the controller 1811 receives signals form sensor 1814 indicating an optimal peak in light arriving back from the retina—the tilting of the light beam may be halted—since such optimal peak may be indicative of light being refocused back towards a vicinity of the macula.

Figure 4C:
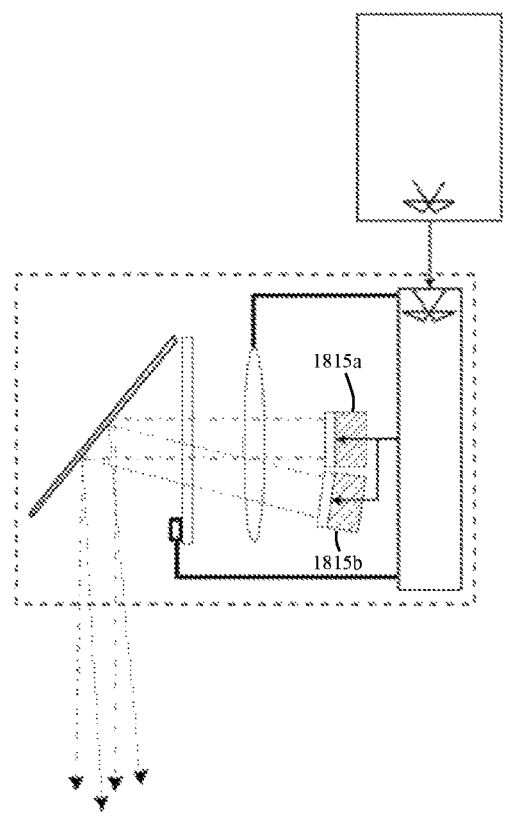

FIG. 4C illustrates an embodiment where an auxiliary optic system may include more than one (here two) light sources 1815a, 1815b. The light sources may be placed already tilted one relative to the other in tilted states anticipating relative movements of the eye during surgery. Such light sources 1815a, 1815b if desired may be controlled also to tilt from their base states in a manner similar to that described herein above.

Controller 1811 may be in communication via for example Bluetooth with a mobile device 1820 such as a tablet that can be used for displaying to the surgeon data relating to auxiliary optic system 181 and/or for allowing the surgeon to control auxiliary optic system 181, e.g. by changing intensities of light source 1815 e.g. by voice activation, touch screen (or the like).

When the surgical procedure to the natural lens of the eye starts (e.g. removal of the eye's natural lens commences), the reduced optical power due to the diminishing natural lens—results in light not being focused on the retina and in particular a vicinity of the macula (see, e.g., FIGS. 3B, 3C). This drastic decrease in brightness may be detected by sensor 1814 as removal of the natural lens.

Determination that the cause for such decrease in brightness is due to lens removal (and not e.g. eye movement)—may be provided by the surgeon performing the surgical procedure that is aware to the surgical stage he/she initiated. The surgeon may e.g. via voice activation provide such feedback to the controller—so that the suitable correction may be performed to compensate for the removed optical power of the removed natural lens.

In certain embodiments, the controller when receiving such inputs from sensor 1814 indicative of removal of the natural lens (or as aforementioned directly from the surgeon), may be programmed to urge the tunable lens 1816 (which initially may be flat and thus with substantially no optical power)—to assume a curvature. Example of such lens 1816 are VectorLens, OptoTune, VariOptic. Such curvature may urge the tunable lens 1816 to assume an optical power that intervenes with incident light arriving from light source 1815 to re-focus the light towards the retina and preferably towards a vicinity of the macula.

Attention is drawn to FIGS. 5A to 5G illustrating embodiments of an integrated optic system 182. FIG. 5A illustrates elements some of which unique to integrated optic system 182 and some of which possibly available in an ophthalmic microscope 12.

An example of an element unique to integrated optic system 182 shown in FIG. 5A may be a unique light source 1825, while a beam splitter 1828 of system 182 may be generally similar to that typically available in an ophthalmic microscope 12, which may be configured to reflect incident light arriving from light source 1825 along an optical axis X of the microscope to exit the microscope via an objective lens 16 of system that is generally similar to those typically available in an ophthalmic microscope 12.

Beam splitter 18288, feedback sensor 18144 and tunable lens 18166 all marked by the dashed lines in FIG. 5A demonstrate optional elements unique to an integrated optic system (such as 182) that may be used for detecting changes in intensity of light retuning from the eye via sensor 18144. Compensating such detected changes may e.g. be performed by focusing outgoing light from light source 1825 via the optional tunable lens 18166, and/or by increasing the intensity of the light source 1825 itself (and then possibly such tunable lens may not be necessary). All other embodiments in FIG. 5 may make use of such elements.

As seen in FIG. 5A incoming light arriving from the microscope along optical axis X towards the eye is arranged (as also explained with respect to FIG. 3A) to be focused, inter alia, by the eye's natural lens towards a vicinity of the macula—where it is scattered back also out of the eye forming the 'red reflex' wave length spectrum that provides the surgeon with background illumination and contrast necessary for visualization of eye elements being treated such as the capsule, lens and anterior chamber structure, during ophthalmic surgery.

FIG. 5B illustrates a state generally similar to that in FIG. 3B, where once removing the natural eye lens at least partially, the focal power of the natural lens formerly assisting in directing light rays towards the retina and in particular the macula—is reduced. This as seen may result in substantially fewer light rays hitting the macula to be scattered back towards the area of the lens being treated in order to illuminate it.

Consequently, the surgeon operating the eye is provided as here seen with lower background illumination that may affect his/her ability to successfully conduct the surgical procedure at stake. Further shown in this figure is that at least some of the incoming light may impact lens' fragments left within the treated eye and scatter away from the macula or absorbed in fragments further reducing visualization for the surgeon.

As seen in FIG. 5C, integrated optic system 182 in at least certain embodiments may be arranged to include an intervening lens 1826 that may be inserted in this example in-between light source 1825 and beam splitter 1812. Intervening lens 1826 may be inserted via a Filter wheel or may be embodied as an electronic lens.

Intervening-lens 1826 may be arranged to interact with incident light arriving from light source 1825 in order to compensate for optical power lost due to removal of eye's natural lens—so that the light emitted by light source 1825 will remain focused towards a vicinity of the macula during stages of a surgical operation where there is substantially no lens present within the lens capsule (i.e. until the intraocular plastic lens is inserted into the lens capsule).

Attention is drawn to FIG. 5D illustrating a situation where the light emitted by light source 1825 may be shifted away from being focused towards a vicinity the macula, due to rotation or e.g. lateral movement of the eye—in this example due to eye rotation. Such eye movement may accordingly move the macula from being aligned with the microscope's optical axis X along which the incoming light travels.

Figure 5E:
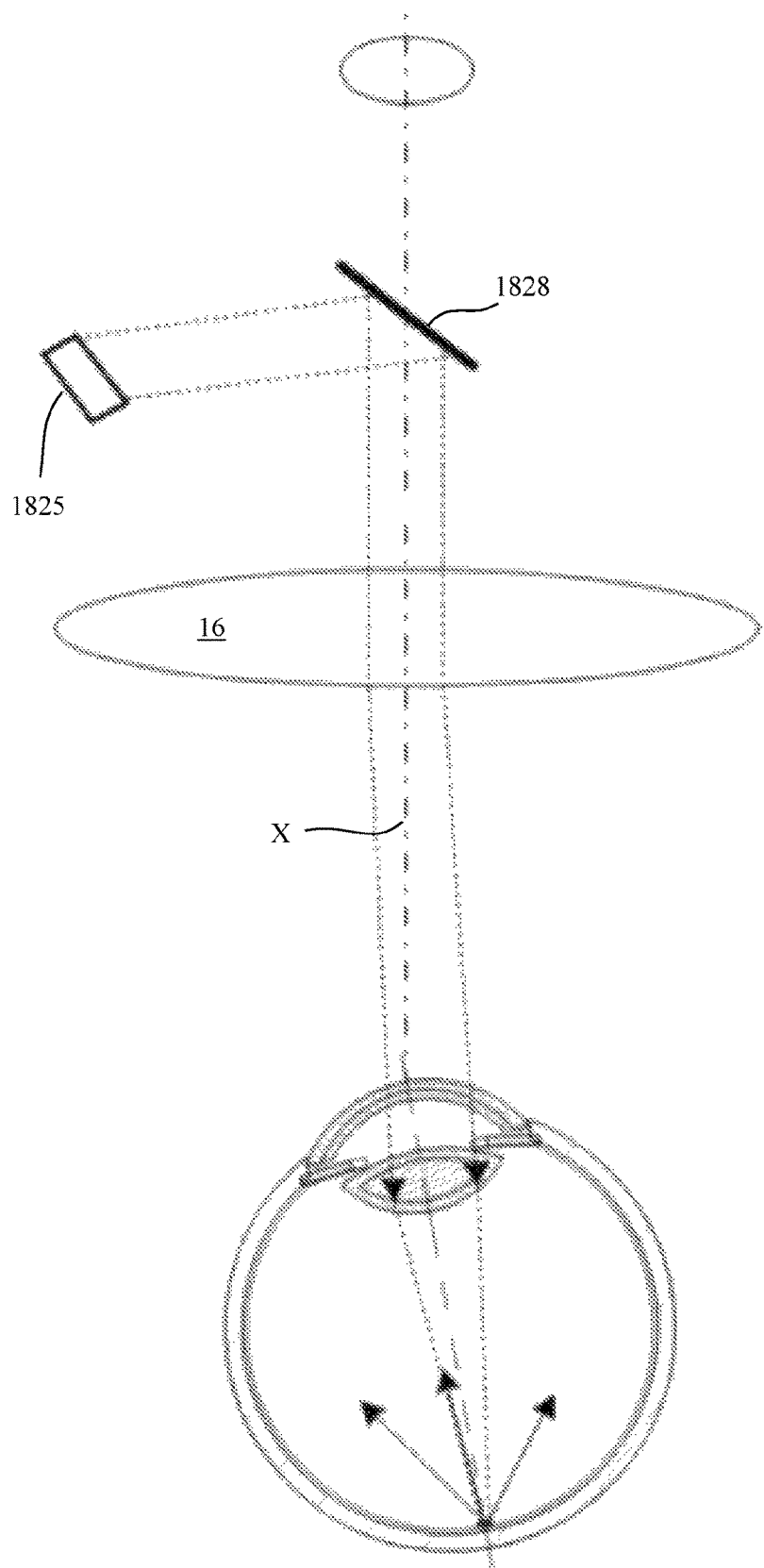

As seen in FIG. 5E, integrated optic system 182 in at least certain embodiments may be arranged to tilt light source 1825 so that incident light arriving from the tilted light source 1825 now travels along an optical path that is re-directed towards a vicinity of the macula (this compensation is generally similar to that depicted with respect to the auxiliary optic system in FIGS. 4A and 4B). Thus, the resumed focus of light at the macula restores the intensity of light scattered back from the macula to illuminate the area of the lens being treated.

Figure 5F:
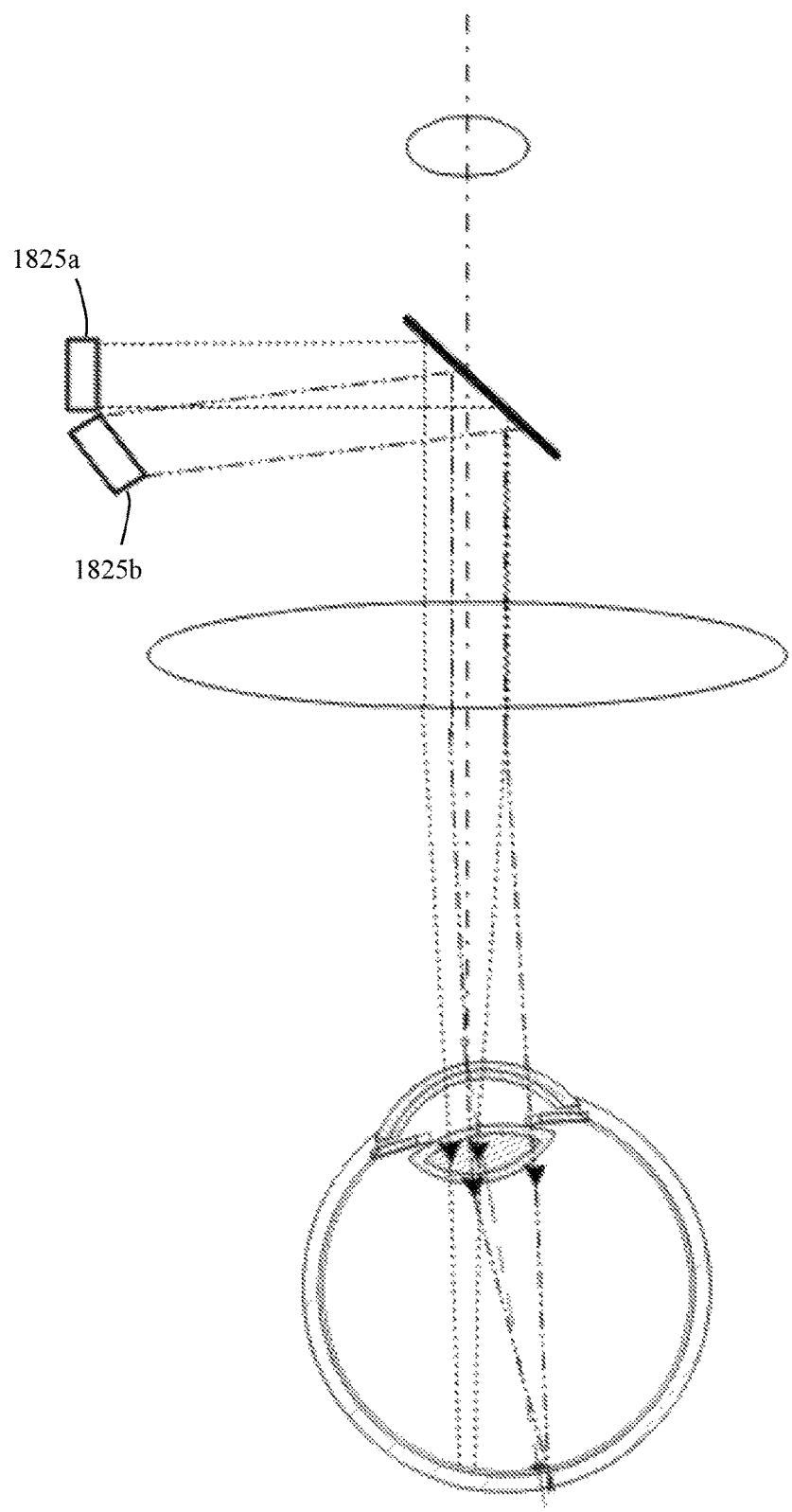

FIG. 5F shows an embodiment generally similar to that shown in FIG. 4C, illustrating how integrated optic system may be provided with more than one (here two) light sources 1825a, 1825b. The light sources may be placed already tilted one relative to the other in tilted states anticipating relative movements of the eye during surgery.

Figure 5G:
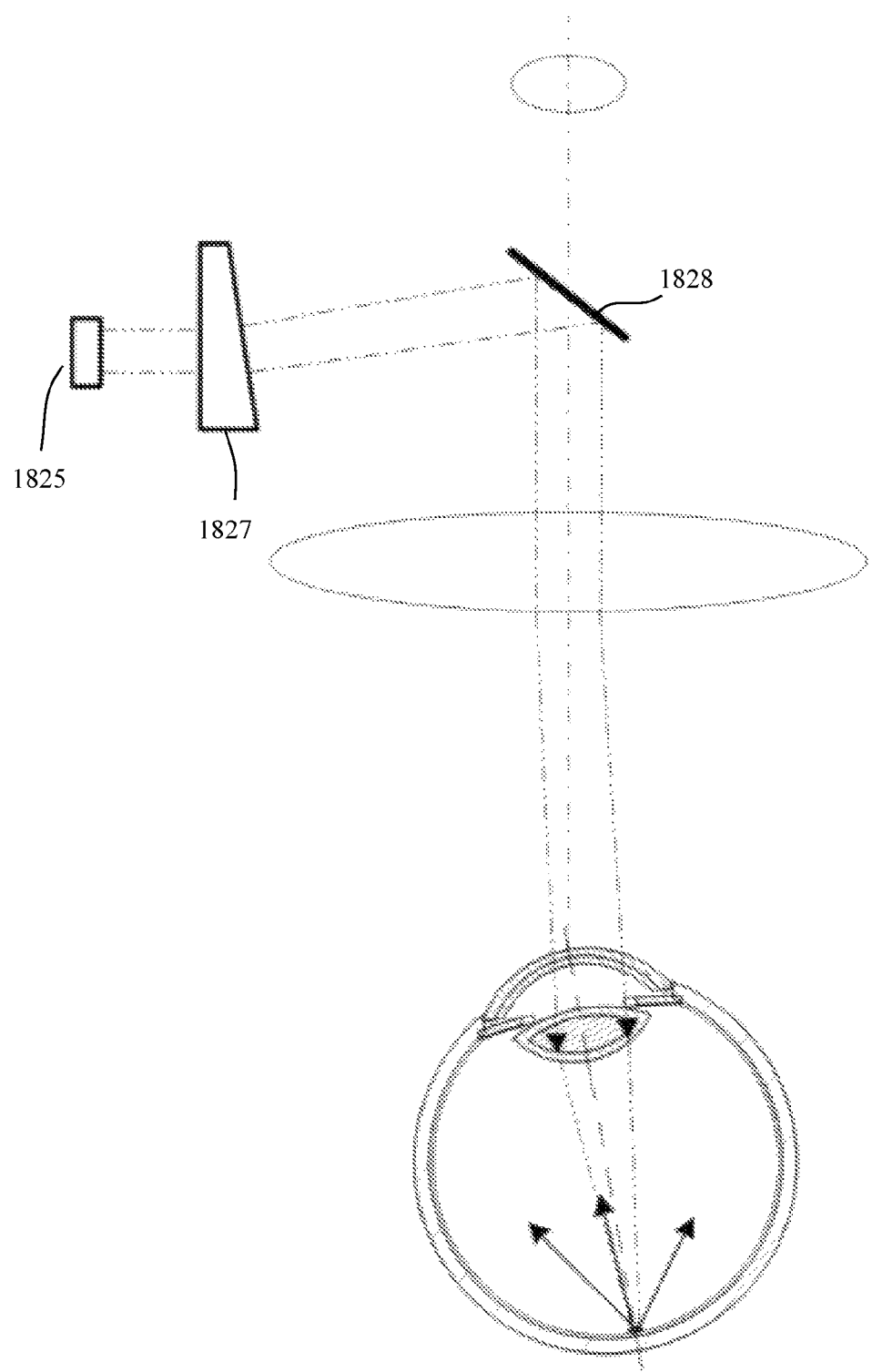

FIG. 5G illustrates an embodiment of an integrated optic system that is arranged to include an intervening wedge like optic 1827 that may be inserted in this example in-between light source 1825 and beam splitter 1812. An electronic beam steering member also can be inserted in the path either by mirror steering or by prism. The wedge like optic may be arranged to compensate for eye movements by tilting and re-directing light towards a vicinity of the macula. Thus, the resumed focus of light at the macula restores the intensity of light scattered back from the macula to illuminate the area of the lens being treated.

Figure 6A:
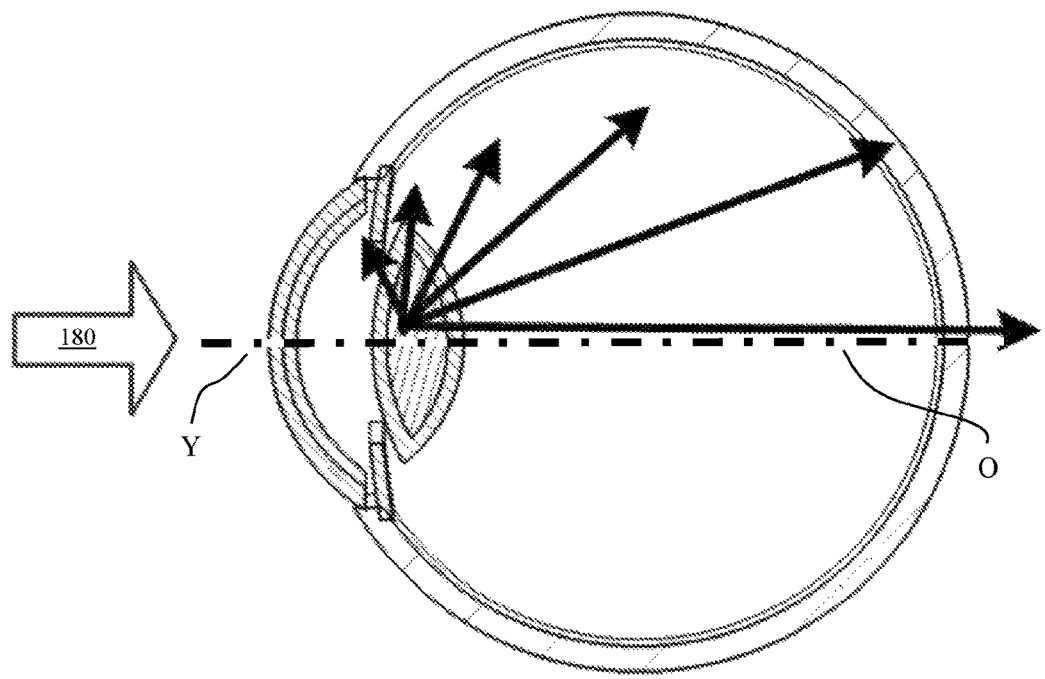
FIGS. 6A and 6B schematically show light rays emitted generally along an axis into an eye and scattered/deflection pattern of the light rays relative to the axis as such rays encounter scattering elements of the eye.
Figure 6B:
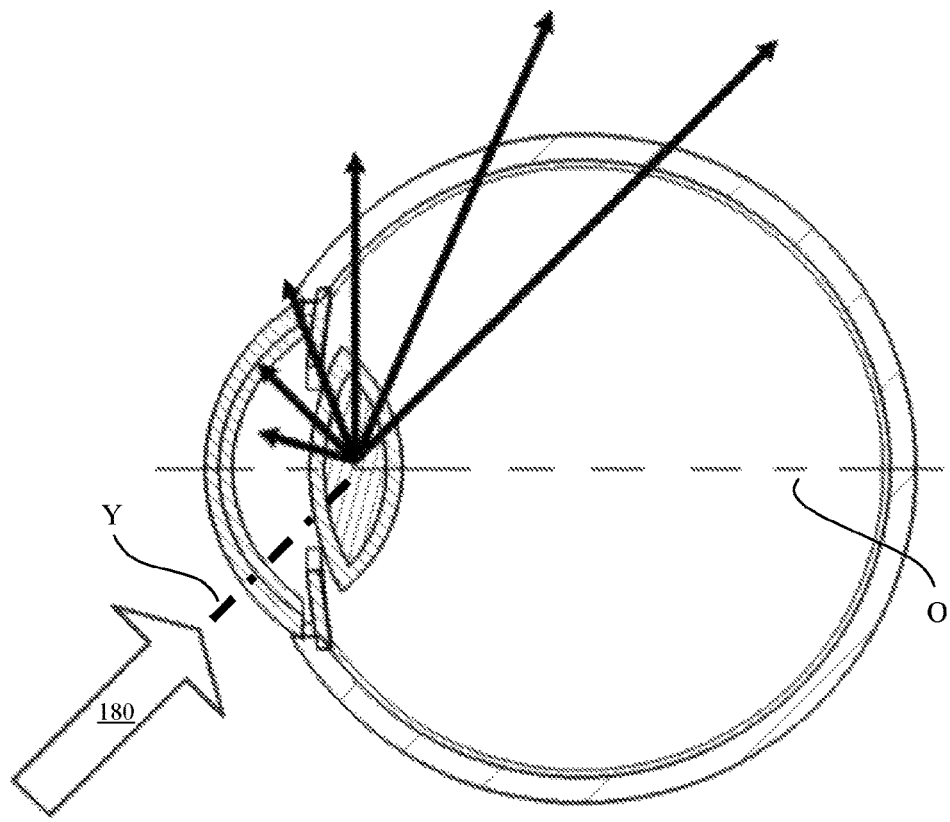

Attention is drawn to FIGS. 6A and 6B illustrating typical scattering patters of light from eye particles/fragments/edges that typically occur when removing a natural lens from the lens capsule. Such scattering of light may be described according to known theories such as the Mie or Rayleigh scattering models.

As seen in these figures, the scattered light forms a pattern that follows an axis Y along which incoming light 180 arrives—in that the vector of scattered light is generally largest along axis Y in the light direction as shown in the arrow 180, while the intensity of scattered light diminishes as it diverges away from axis Y.

Therefore, when incoming light as seen in FIG. 6A arrives along an axis Y that generally coincides with an optical axis O of an eye—most of the scattered light will be directed into the eye with substantially almost no scattered light being directed out of the eye. However, when the incoming light as seen in FIG. 6B arrives along an axis Y that is angled relative to the eye's optical axis O—some of the scatted light may escape out of the eye. Such scattered light in accordance with various embodiments of the invention may be utilized to reveal structures in the eye lens, capsule (etc.) that otherwise may be difficult to observe.

Attention is drawn to FIGS. 7 to 10 illustrating illumination module embodiments 190, 191, 192 according to an aspect of the present invention, which are intended to be placed closely adjacent to an eye in order to illuminate the eye and in particular a vicinity of the eye's lens during surgical procedures where the natural lens of the eye is removed.

Such illumination module embodiments 190, 191, 192 may possibly be used in conjunction with existing microscope illumination or the integrated and auxiliary optic system embodiments described herein above—and may be useful in particular during stages of optical surgery where the part of the front capsule is removed and the natural lens is being breached and removed, stages during which there may be an increased formation of particles/fragments/folds within elements of the eye such as the lens, lens capsule (etc.)

Figure 7A:
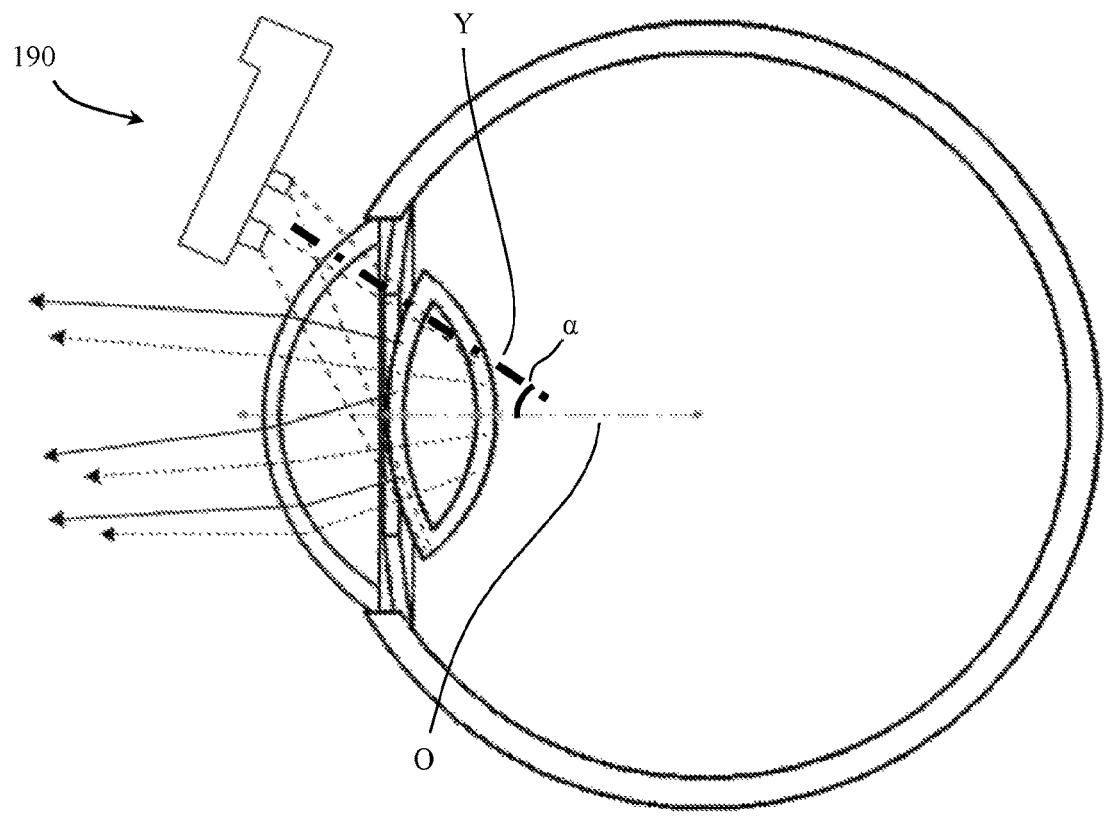
FIGS. 7A, 7B, 8A, 8B, 9A to 9C, 10A to 10D, 11A, 11B and 12A to 12C schematically show illumination modules for illuminating elements of an eye, possibly forming part and/or working in conjunction with integrated or auxiliary system embodiments of the invention.
Figure 7B:
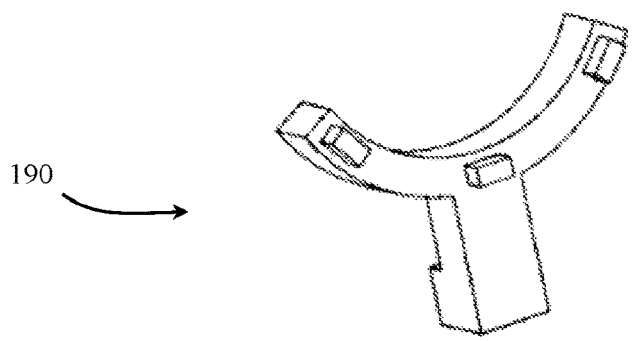
Figure 8A:
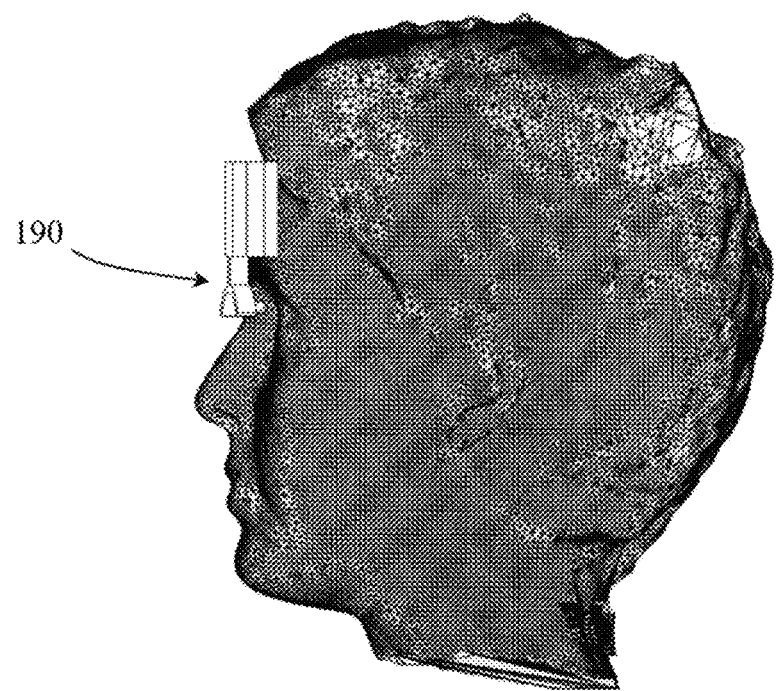
Figure 8B:
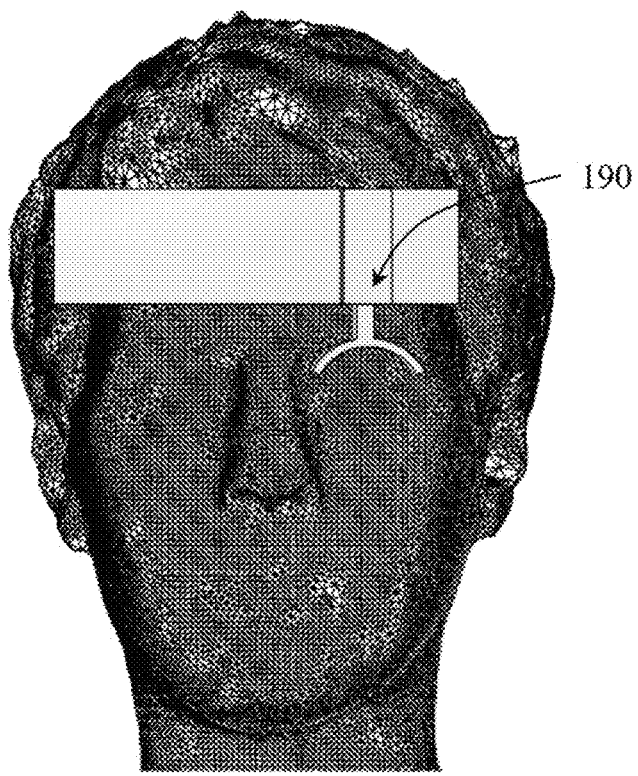

The illumination module 190 seen in FIGS. 7A and 7B embodies an option where light sources used may be LED's; and the illumination module 191 seen in FIGS. 8A to 8C embodies an option where light sources used may be communicated towards the eye by optic fibers or light guides from a light source further upstream.

As seen in these figures, the angled axis Y along which light is emitted into the eye relative to the eye's optical axis O—allows some light being scattered off fragments formed within the eye or folds in the capsule—to escape out of the eye to be picked up by e.g. a microscope (here not shown) through which a surgeon observes the eye during surgery.

FIGS. 8A and 8B illustrate an option of fitting an illumination module adjacently to an eye being treated, here by attaching the module to a forehead region of a patient. In this example the illumination module is the LED based option 190, however other types of modules disclosed herein may equally be fitted in this matter to the patient.

Figure 9A:
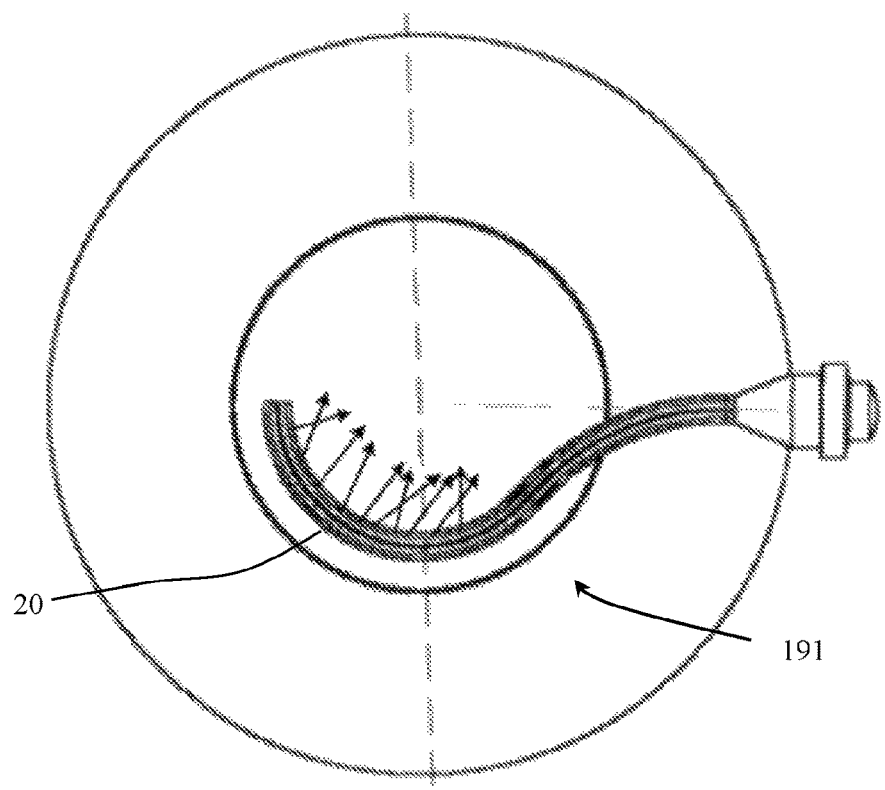
Figure 9B:
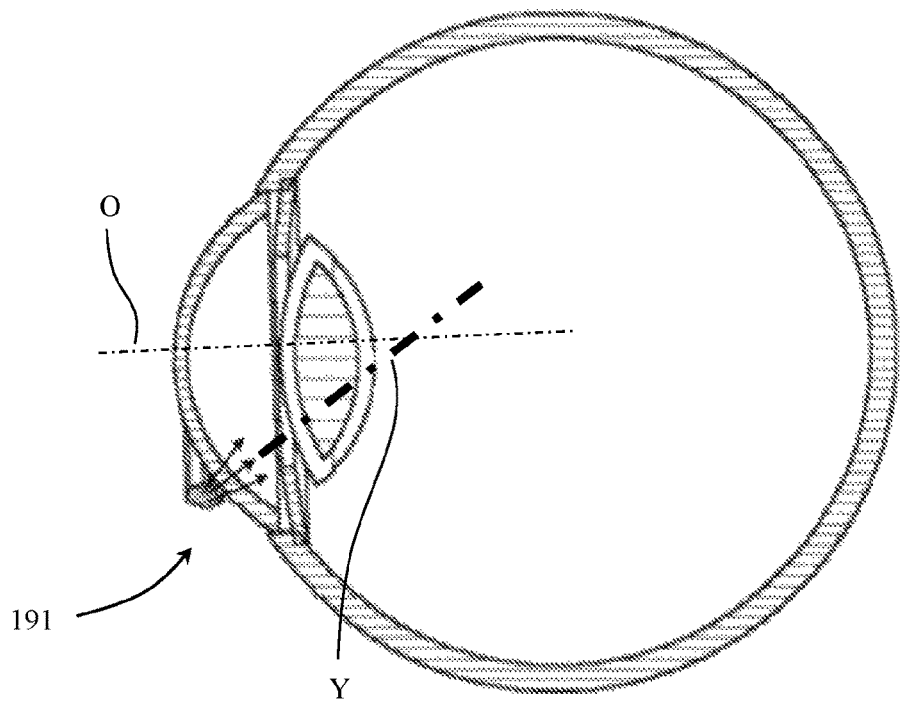

The illumination module of FIGS. 9A and 9B illustrates an embodiment where a light guide may be used in at least certain illumination module embodiments 191 for illuminating the eye. Illumination module 191 is here seen comprising a curved section 20 circling a portion of the eye and emitting light rays along axes Y that are transverse to an optical axis o of the eye. The light source can be for example LED or Light guide or fiber optic. In certain cases, (see FIG. 9C) illumination module 191 may be embodied as one or more optical fibers that may be inserted to within the eye for illuminating the eye e.g. lens from extreme closeness.

FIGS. 10A to 10D illustrate an illumination module embodiments 192 possibly similar to that shown and disclosed with respect to FIG. 9 (but not necessarily). Illumination module 192 may be defined as an add-on to a speculum.

Figure 10A:
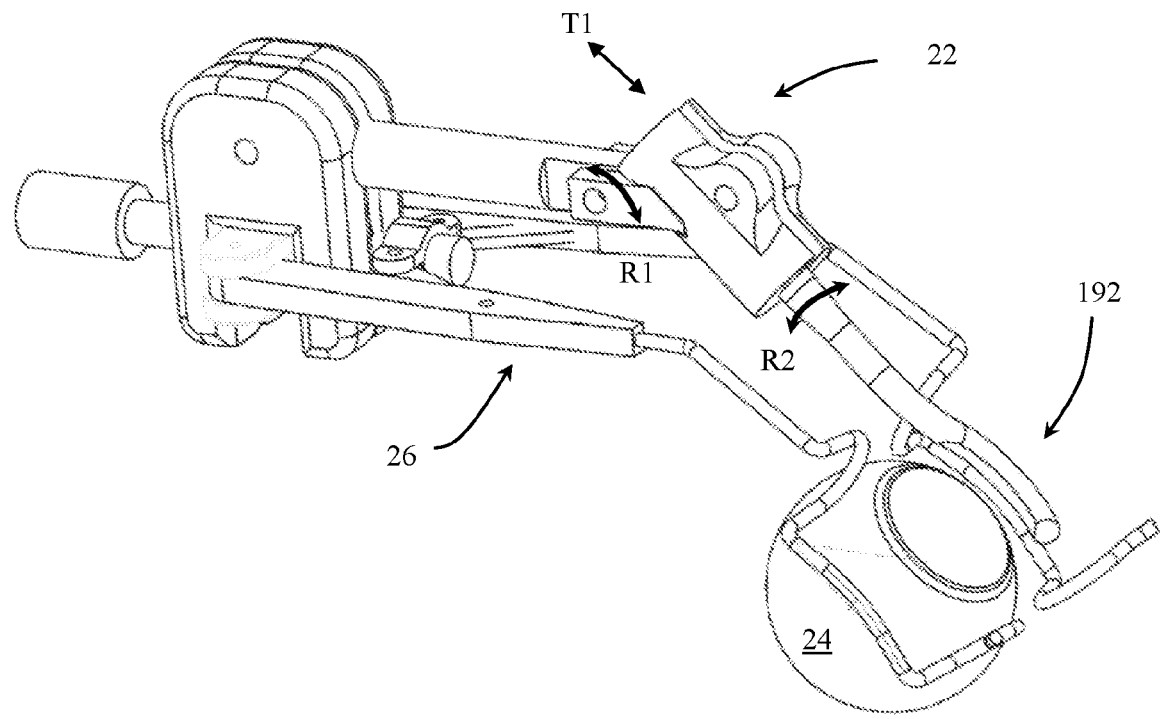
Figure 10B:
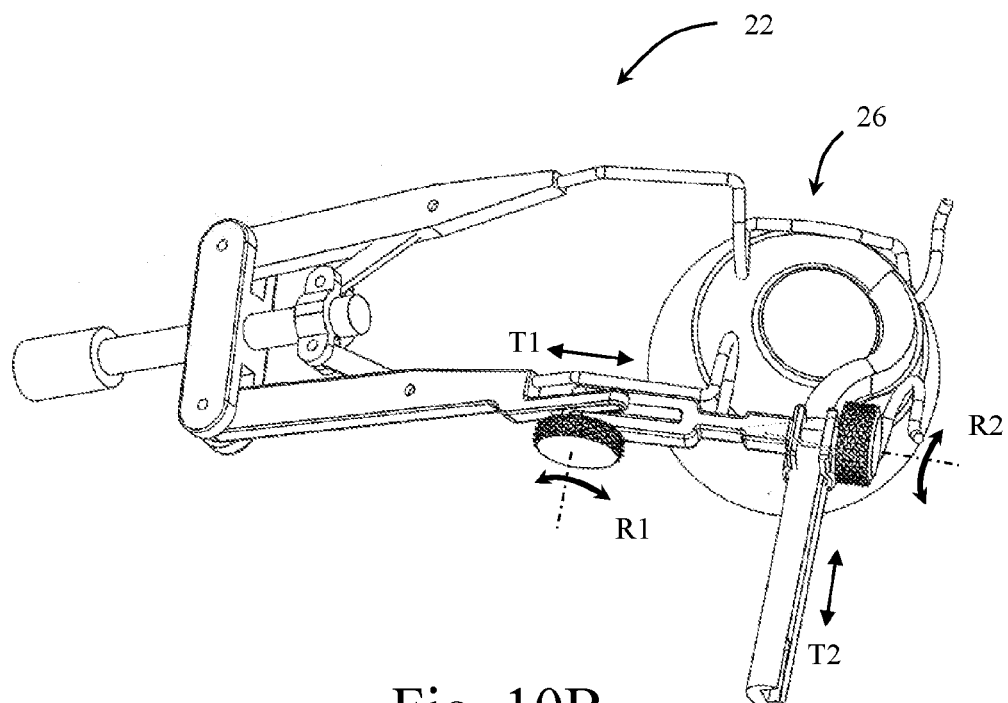

Illumination module 192 in FIGS. 10A and 10B is shown fitted to an articulating member 22 in order to control direction of light emitted from the module to specific locations within an eye 24. Articulating member 22 may provide several degrees of freedom for adjustment of the illumination module relative to the eye, where in this example this may be seen as including two rotational components R1, R2 and one linear translation component T1 in FIG. 10A and two linear translation component T1, T2 in FIG. 10B. It is noted that illumination module 192 may be mounted to various locations of a patient's head adjacent the eye, such as to a forehead or an eye speculum.

Articulating member 22 in this example can also be seen including an eye speculum 26 that may be used for retracting the eyelid during ophthalmic surgery.

In an aspect of the preset invention, fitting various illumination module embodiments to an articulating member, either by coupling such illumination module(s) to a distinct articulating member such as 22 here shown, or by integrally forming such illumination module(s) with an articulating member generally similar to 22 (see e.g., FIG. 10B where an example of an integral speculum device that is used both as an eyelid opener and as an articulating arm is shown)—may facilitate targeting emitted light from such module(s) to be substantially aimed at a region of an eye lens being removed (e.g. during cataract surgery).

Figure 9C:
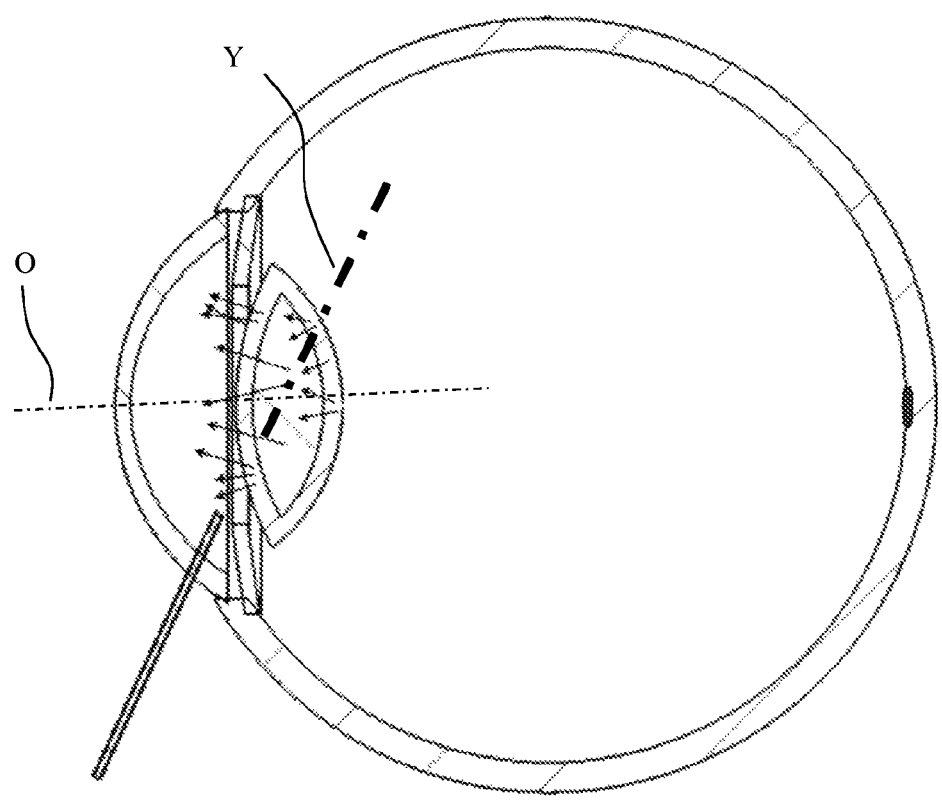

Such targeting of the emitted light as seen, e.g. in FIGS. 7A, 9B, 9C—is accordingly aimed at illuminating lens fragments possibly not yet removed from the eye—so that substantially all such fragments may be removed prior to implanting a plastic lens into the eye. In certain cases, such targeting of the emitted light may comprise emitting light along an axis Y that forms an internal angle $\alpha$ (see indicated in FIG. 7A) that may be less than about 45 degrees.

Figure 10C:
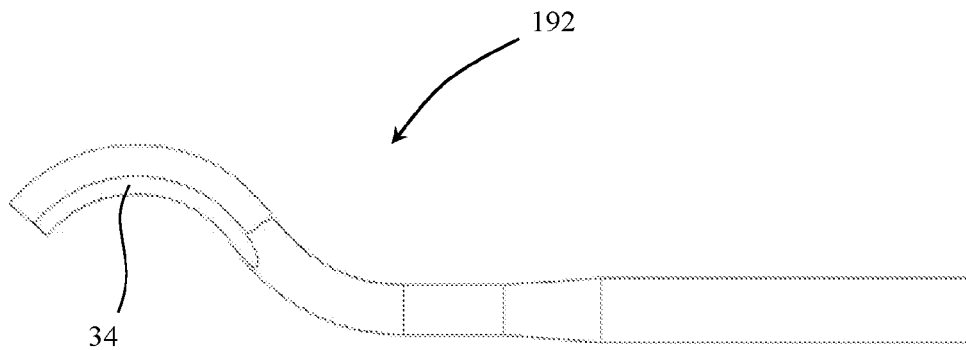
Figure 10D:
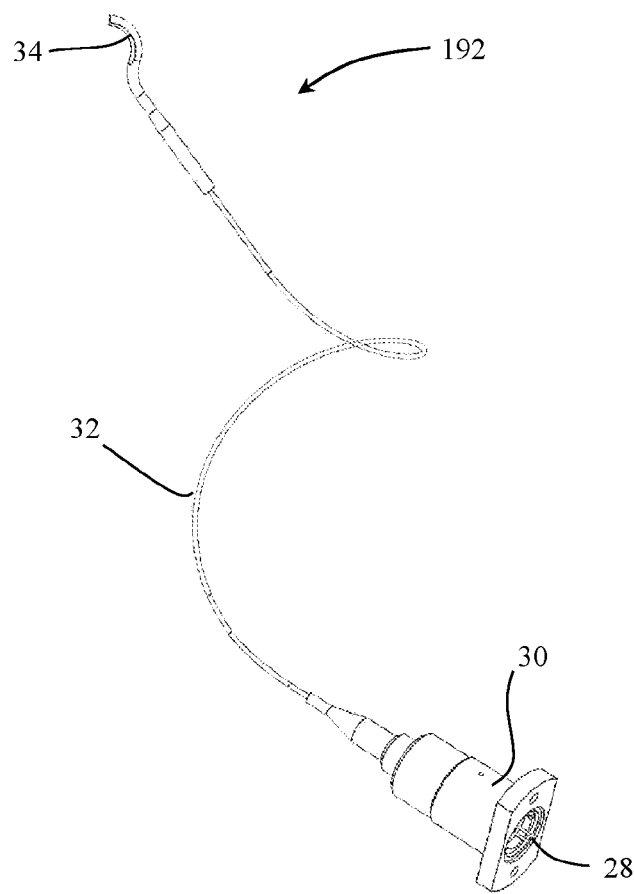

FIG. 10C demonstrates an embodiment where an illumination module, here 192, may be arranged to receive incoming light from a laser diode 28 that is directed by focusing optics 30 through optical fiber(s) 32 towards the illumination module, where it may be emitted towards the eye via a light emitting area 34 of the module. FIG. 10C provides an enlarged view of illumination module 192 including its light emitting area 34.

In experimental tests conducted for various illumination module embodiments of the present disclosure, it has been found that illumination module embodiments utilizing blue light source(s) for illuminating an eye—have been found to enhance image details and increase e.g. by about 50% the resolution apparent to the surgeon (e.g. increase the ability to detect details of about 15 micron in size from about 30 micron in size under red light background illumination scattered from the retina).

Such light sources emitting light in the blue wavelength may be optimal for increasing visualization of elements within the eye such as the eye lens and/or fragments of or within an eye lens when the lens is being removed (or the like), since such wave length may be generally similar to or larger than the eye particle size a physician would like to observe within the eye.

In an aspect of the present invention, "optimization" may be provided to an angle of incidence at which light may be emitted towards a lens region of an eye by various illumination module embodiments. Such "optimization" may be aimed at providing a surgeon with enhanced visualization of the lens region (e.g. lens fragments possibly not yet removed from an eye during cataract surgery). In a preferred embodiment, such optimization may be to light emitted in the blue light range, for example between about 400 and about 495 nanometers, from illumination module embodiments described herein.

Figure 11A:
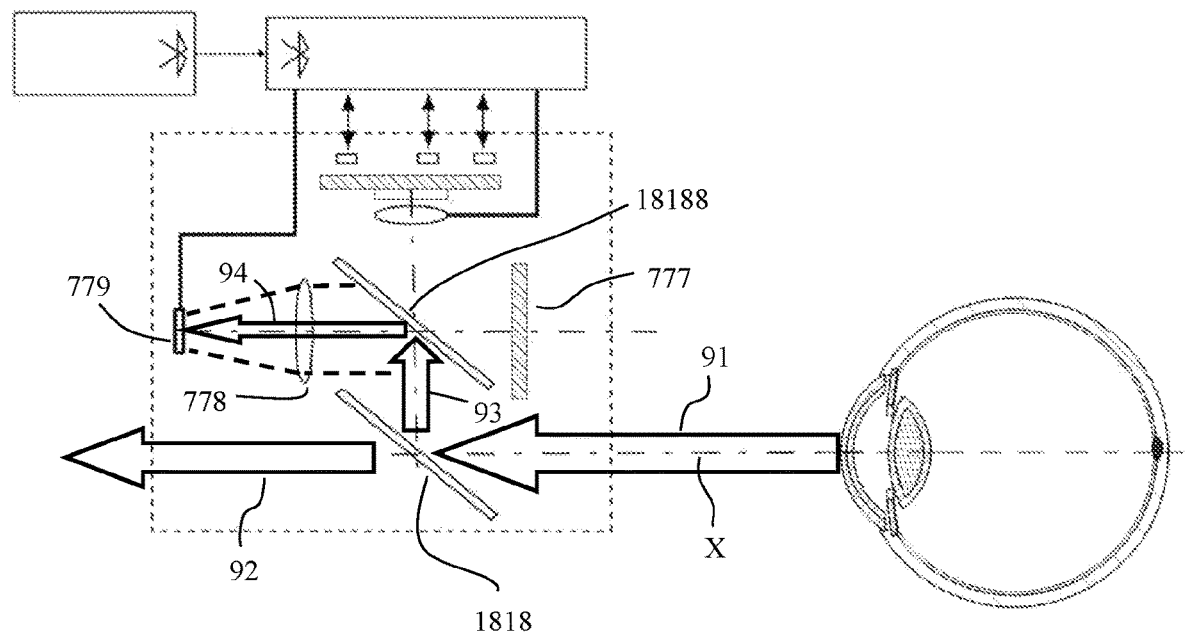
Figure 11B:
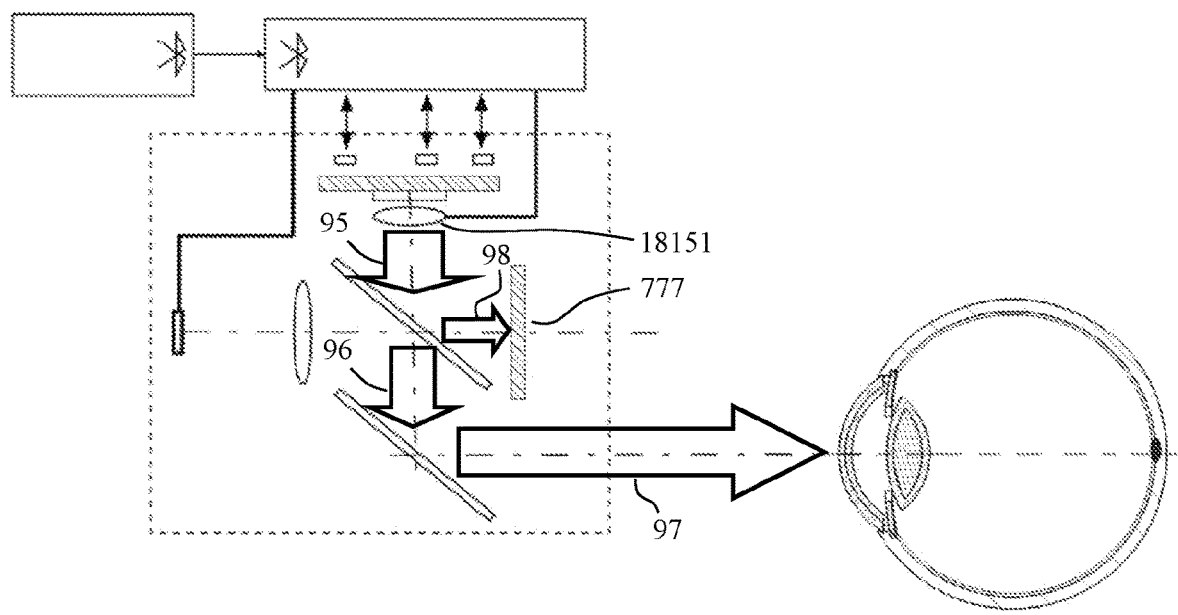

Attention is drawn to FIGS. 11A and 11B illustrating one example of how such "optimization" may be accomplished. The example here shown illustrates assistance being provided for the "optimization" by an embodiment of an 'auxiliary' type optic system, however "optimization" concepts here demonstrated may be equally provided by an 'integral' type optic system or may be integrated into at least some illumination module embodiments.

The 'auxiliary' type optic system here illustrated may be generally similar to that shown e.g. in FIG. 4A—and may be provided with a secondary beam splitter 18188 in addition to beam splitter 1818. The system may additionally be provided with an optional light absorber 777, a focusing lens 778 and a light sensor 779.

FIG. 11A illustrates a possible "optimization" sequence in which light emitted towards a lens region by an illumination module (such as any one of the illumination modules seen in FIGS. 7 to 10), may be scattered off the lens region to form a path 91 along an optical axis X of a microscope used for observing the eye. Light 91 meets beam splitter 1818—where a portion thereof 92 passes onwards along axis X towards the microscope, while another portion thereof 93 is reflected by beam splitter 1818 into the system. Light 93 meets secondary beam splitter 18188 where a portion thereof 94 may be reflected via a possible focusing lens 778 towards light sensor 779.

In an embodiment of the present invention, signals received by light sensor 779 may be used for computing/assessing an "optimized" angle at which light may be emitted by an illumination module (such as that shown in FIG. 10A) towards a lens region of an eye. A surgeon using an embodiment of an illuminating module for illuminating a lens region of an eye—may adjust the angular direction at which the light is emitted towards the eye lens according to the signals picked up by sensor 779.

FIG. 11B illustrates use of this type 'auxiliary' optic system for illuminating the eye (in a similar manner to that already discussed with respect e.g. to FIG. 4A). Light 95 emitted by a light source 18151 of the system may be arranged to initially follow a route that may be transverse (e.g. generally orthogonal) to optical axis X.

A portion thereof 96 passing through secondary beam splitter 18188 may then be reflected by beam splitter 1818 along axis X to form a light path 97 towards the eye for creating the 'red reflex' phenomena providing background illumination of eye elements. Some of the light 98 reflected by secondary beam splitter 18188 may be blocked by light absorber 777 is so desired.

Figure 12A:
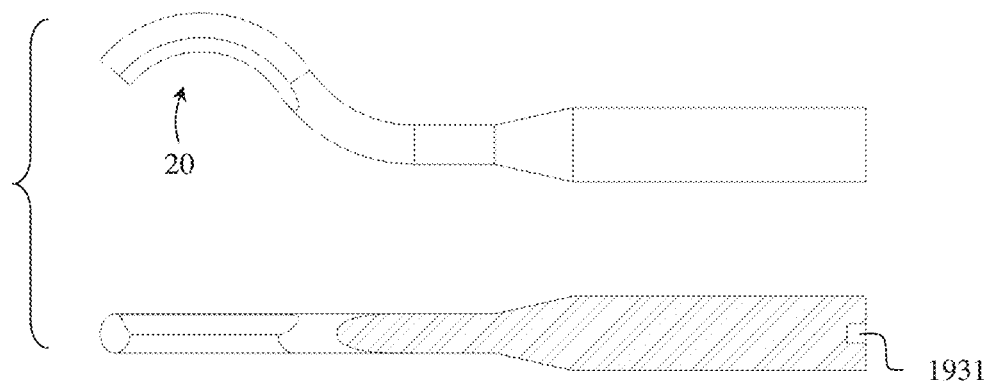
Figure 12B:
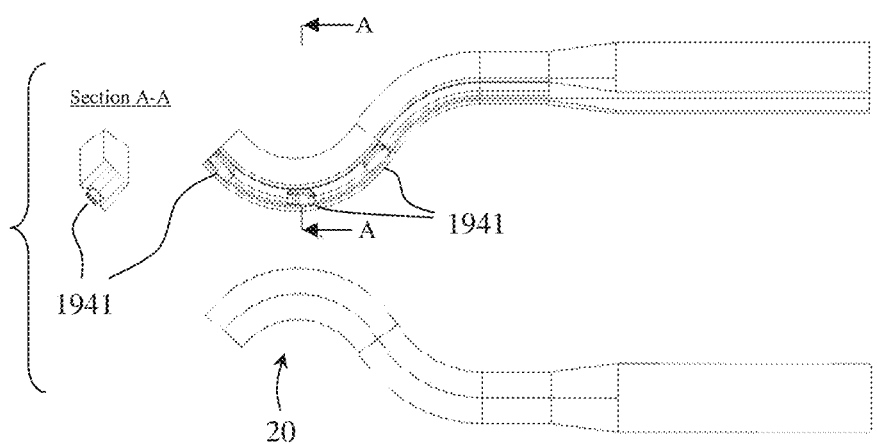
Figure 12C:
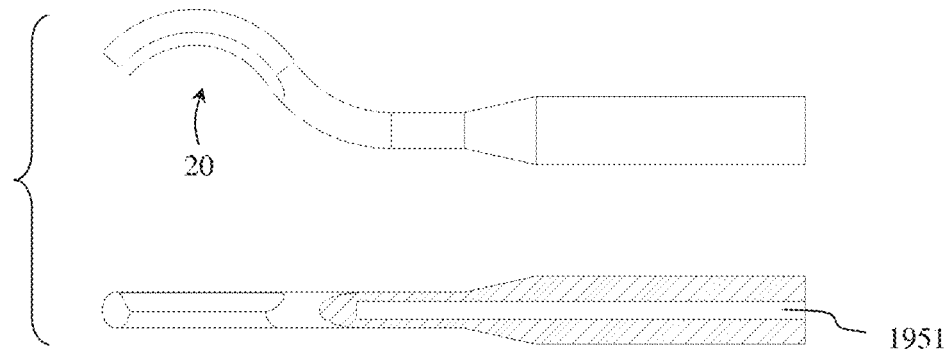

Attention is drawn to FIGS. 12A to 12C illustrating various illumination module embodiments. Illumination module 193 includes a housing 1931 at its proximal side arranged to house a LED, wherein light emitted by the LED may then be channeled via the illumination module to its curved section 20 to be emitted from there towards the eye's lens region. Illumination module 195 includes an axially extending passage 1951 from receiving an optical fiber through which light can be transferred to be emitted from the module's curved emitting section 20.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. An auxiliary optic system for use outside of a visualization device the visualization device being suitable for observing eye elements during surgery along an optical axis, the auxiliary optic system comprising:
   optic devices aimed at affecting visualization of the eye elements by the visualization device by:
   selecting a wave-length spectrum of light of between about 420 to about 750 nanometers to be emitted towards the eye from a light source of the auxiliary optic system along a light path; and changing an optical power by which the light emitted towards the eye from the light source along the light path converges;

wherein the auxiliary optic system comprises a beam splitter intercepting the optical axis-X of the visualization device for reflecting at least part of the light emitted by its light source to extend coaxially along the optical axis of the visualization device towards the eye;

wherein the changing of the optical power is by introducing a lens into the light path before it reaches the beam splitter from the light source, and wherein the interception of the optical axis of the visualization device is along a section of the optical axis between the objective lens of the visualization device and the eye being observed.

2. The auxiliary optic system of claim 1, wherein the affecting of visualization of the eye elements by the visualization device is also by tilting a light path of light emitted towards the eye, wherein the tilting the light path comprises tilting a light source emitting light towards the eye.

3. The auxiliary optic system of claim 1, wherein tilting the light path comprises using a different light source for illuminating the eye and/or inserting a prism or a mirror into the light path.

4. The auxiliary optic system of claim 1, wherein changing the optical power comprises urging change in a diopter of a lens through which the light path already passes.

5. The auxiliary optic system of claim 1 and being arranged to intervene with the optical axis of the visualization device by urging the beam splitter to intercept the optical axis of the visualization device.

6. The auxiliary optic system of claim 1 comprising and/or being used in conjunction with an illumination module placed closely adjacent to the eye for emitting light towards the eye along an axis that is angled relative to an optical axis of the eye.

7. The auxiliary optic system of claim 6, wherein light emitted by the illumination module is in a blue light range, for example between about 400 and about 495 nanometers.

8. The auxiliary optic system of claim 6, wherein the illumination module comprising at least a portion that is inserted to extreme closeness of the eye, for example an optical fiber.

9. The auxiliary optic system of claim 1, wherein the visualization device is any one of: an ophthalmic microscope, a surgical digital microscope, a 3D video digital microscope and/or video microscope.

10. A visualization device suitable for observing eye elements during surgery along an optical axis-X and comprising:

an integrated optic system for enhancing visualization, the integrated optic system comprising optic devices aimed at affecting visualization of the eye elements by the visualization device by:

selecting a wave-length spectrum of light of between about 420 to about 750 nanometers to be emitted towards the eye from a light source thereof along a light path, and by changing an optical power by which the light emitted towards the eye from the light source along the light path converges, wherein the integrated optic system is located within the visualization device upstream of an objective lens of the visualization device in a direction away from the eye and comprises:

a beam splitter that is arranged to intercept with the optical axis of the visualization device in order to reflect at least part of the light emitted by the light source coaxially along the optical axis towards the observed eye, and wherein the changing of the optical power comprises introducing a lens into the light path before it reaches the beam splitter from the light source, wherein the affecting of visualization of the eye elements by the visualization device comprises also tilting the light path of light emitted towards the eye by the light source.

11. The visualization device of claim 10, wherein changing the optical power comprises urging change in a diopter of a lens through which the light path already passes.

12. The visualization device of claim 10 and being any one of: an ophthalmic microscope, a 3D surgical digital microscope, a video microscope.

13. The visualization device of claim 10, wherein tilting the light path comprises tilting the light source emitting light towards the eye.

* * * * *